United States Patent
Chatelier et al.

(10) Patent No.: US 9,632,054 B2
(45) Date of Patent: Apr. 25, 2017

(54) SYSTEMS AND METHODS FOR HIGH ACCURACY ANALYTE MEASUREMENT

(75) Inventors: Ronald C. Chatelier, Bayswater (AU); Alastair M. Hodges, Blackburn (AU)

(73) Assignee: Cilag GmbH International, Switzerland (CH)

( * ) Notice: Subject to any disclaimer, the term of this patent is extended or adjusted under 35 U.S.C. 154(b) by 765 days.

(21) Appl. No.: 13/824,308

(22) PCT Filed: Dec. 31, 2010

(86) PCT No.: PCT/US2010/062629
§ 371 (c)(1),
(2), (4) Date: Aug. 1, 2013

(87) PCT Pub. No.: WO2012/091728
PCT Pub. Date: Jul. 5, 2012

(65) Prior Publication Data
US 2013/0306493 A1   Nov. 21, 2013

(51) Int. Cl.
G01N 27/327 (2006.01)
C12Q 1/02 (2006.01)
(52) U.S. Cl.
CPC ........... G01N 27/327 (2013.01); C12Q 1/025 (2013.01); G01N 27/3274 (2013.01)
(58) Field of Classification Search
CPC ..................................... G01N 27/327–27/3274
See application file for complete search history.

(56) References Cited

U.S. PATENT DOCUMENTS

| | | | |
|---|---|---|---|
| 5,719,034 A | 2/1998 | Kiser et al. | |
| 6,193,873 B1 | 2/2001 | Ohara et al. | |
| 6,391,645 B1 * | 5/2002 | Huang | C12Q 1/006 422/82.02 |
| 1,455,258 A1 | 9/2005 | Pugh | |
| 7,195,704 B2 * | 3/2007 | Kermani | G01N 27/3274 205/775 |

(Continued)

FOREIGN PATENT DOCUMENTS

| | | |
|---|---|---|
| CN | 1284652 A | 2/2001 |
| CN | 1455258 A | 11/2003 |

(Continued)

OTHER PUBLICATIONS

International Search Report/Written Opinion for PCT Application No. PCT/US2010/062629; mailed Feb. 23, 2011; 9 pages.

(Continued)

*Primary Examiner* — Alexander Noguerola
(74) *Attorney, Agent, or Firm* — Barclay Damon, LLP

(57) ABSTRACT

Methods for determining a concentration of an analyte in a sample, and the devices and systems used in conjunction with the same, are provided herein. In one exemplary embodiment of a method for determining a concentration of an analyte in a sample, a sample including an analyte is provided in a sample analyzing device having a working and a counter electrode. An electric potential is applied between the electrodes and a first analyte concentration is determined. A second analyte concentration value is calculated from the first analyte concentration value and corrected for temperature effects, fill time and capacitance to provide for a final analyte concentration value.

21 Claims, 12 Drawing Sheets

(56) References Cited

U.S. PATENT DOCUMENTS

| | | | |
|---|---|---|---|
| 7,338,639 B2 | 3/2008 | Burke et al. | |
| 7,771,583 B2 | 8/2010 | Diamond et al. | |
| 8,163,162 B2 | 4/2012 | Chatelier et al. | |
| 8,551,320 B2 | 10/2013 | Hodges et al. | |
| 2004/0045821 A1* | 3/2004 | Cui | B01L 3/502715 204/403.02 |
| 2004/0203137 A1* | 10/2004 | Hodges | C12Q 1/004 435/287.2 |
| 2006/0175205 A1 | 8/2006 | Cui et al. | |
| 2007/0074977 A1 | 4/2007 | Guo et al. | |
| 2007/0227912 A1* | 10/2007 | Chatelier | A61B 5/1486 205/792 |
| 2009/0123335 A1 | 5/2009 | Nakamura et al. | |
| 2009/0301899 A1 | 12/2009 | Hodges et al. | |
| 2010/0167386 A1 | 7/2010 | Miller et al. | |
| 2010/0173396 A1 | 7/2010 | Miller et al. | |
| 2010/0270178 A1 | 10/2010 | Guo et al. | |
| 2011/0073493 A1* | 3/2011 | Chatelier | G01N 33/5438 205/777.5 |

FOREIGN PATENT DOCUMENTS

| | | | |
|---|---|---|---|
| EP | 1 422 523 A1 | 5/2004 | |
| JP | 2006-215034 | 8/2006 | |
| JP | 2007-121060 | 5/2007 | |
| JP | 2007-271622 | 10/2007 | |
| JP | 2008-510154 | 4/2008 | |
| JP | 2009-294213 | 12/2009 | |
| JP | 2010-504524 | 2/2010 | |
| RU | 2 263 904 C2 | 11/2005 | |
| WO | WO 02/06806 A2 | 1/2002 | |
| WO | WO 2006/018425 A2 | 2/2006 | |
| WO | WO 2008/036516 A1 | 3/2008 | |
| WO | WO 2008040990 A2 * | 4/2008 | G01N 33/487 |
| WO | WO 2008/150436 A1 | 12/2008 | |

OTHER PUBLICATIONS

Chinese Office Action and Search Report for CN 201080071267.X; dated Sep. 2, 2014; 17 pages.
Russian Office Action for: RU 2013135711; dated: Sep. 22, 2014; 14 pages.
Japanese Office Action for JP 2013-547447; dated: Feb. 24, 2015; 1 page.
Chinese Office Action for CN 201080071267.X; dated May 11, 2015; 5 pages.
Chinese Office Action for CN 201080071267.X; dated Nov. 6, 2015; 5 pages.
Australian Patent Examination Report for AU 2010366640; dated: Nov. 19, 2015;3 pages.
In vitro diagnostic test systems—Requirements for blood-glucose monitoring systems for selftesting in managing diabetes mellitus; GOSR R ISO 15197-2009; Russian Federation National Standard; (approved and set in force by the Federal Agency on Technical Regulation and Metrology Order of Sep. 12, 2009 No. 619-st); enactment date is Sep. 1, 2010.
High sensitivity C-reactive protein (hsCRP ELISA); Registration Certificate FC No. 2009/04987 of Aug. 31, 2009; Biomerica, Inc.; http://www.analytica.ru/instructions/immunochemistry/ifa/kts/Biomerical/biomerica-7033-crp-utlra.pdf.
Korean Office Action for KR 10-2013-7020051; dated: Sep. 29, 2016; 3 pages.
Japanese Office Action for JP 2015-217551; dated: Sep. 27, 2016; 5 pages.
Handheld Impedance Based Biosensor System for Glucose Monitoring; Amir Mohsen Aliakbar; Aug. 1, 2009; http;//digitool.library.mcgill.ca/thesisfile66772.pdf; 70 pgs.
Factors Affecting Blood Glucose Monitoring Sources of Errors in Measurement; Barry H. Ginsberg, M.D., Ph.D; Journal of Diabetes Science and Technology; vol. 3, Issue 4, Jul. 1, 2009; pp. 903-913; 11 pgs.
Extended European Search Report for EP 10 861 493.4; dated Dec. 19, 2016; 10 pgs.

* cited by examiner

SYSTEMS AND METHODS FOR HIGH ACCURACY ANALYTE MEASUREMENT

CROSS-REFERENCE TO RELATED APPLICATION

This application is a national stage application pursuant to 35 U.S.C. §371 of PCT Application No. PCT US2010/062629, filed Dec. 31, 2010, the entire contents of which are herein incorporated by reference.

FIELD

The system and method provided herein relates to the field of medical testing, in particular the detection of the presence and/or concentration of an analyte(s) within a sample (e.g., physiological fluids including blood).

BACKGROUND

Analyte concentration determination in physiological fluids (e.g., blood or blood derived products such as plasma) is of ever increasing importance in today's society. Such assays find use in a variety of applications and settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like. In response to this growing importance of analyte detection, a variety of analyte detection protocols and devices for both clinical and home use have been developed. Some of these devices include electrochemical cells, electrochemical sensors, hemoglobin sensors, antioxidant sensors, biosensors, and immunosensors.

A common method for analyte concentration determination assays is based on electrochemistry. In such methods, an aqueous liquid sample is placed into a sample reaction chamber in a sensor, e.g., an electrochemical cell made up of at least two electrodes, i.e., a working electrode and a counter electrode, where the electrodes have an impedance that renders them suitable for amperometric or coulometric measurement. The component to be analyzed is allowed to react with a reagent to form an oxidizable (or reducible) substance in an amount proportional to the analyte concentration. The quantity of the oxidizable (or reducible) substance present is then estimated electrochemically and related to the analyte concentration in the sample.

One characteristic of blood that can affect analyte detection is the haematocrit. Levels of haematocrit can be vastly different amongst various people. By way of non-limiting example, a person suffering from anemia may have a haematocrit level of approximately 20% while a neonate may have a haematocrit level of approximately 65%. Even samples taken from the same individual over a period of time can have different haematocrit levels. Further, because high haematocrit can also increase the viscosity of blood, and viscosity can in turn affect other parameters associated with analyte detection, accounting for the effect of haematocrit on a sample can be important in making accurate analyte concentration determinations.

One way in which varying levels of haematocrit in a blood sample have been accounted for is by separating the plasma from the blood and then recalculating the concentration of the antigen with respect to the adjusted plasma volume. Separation has been achieved, for example, by performing a centrifugation step. Other ways in which the varying levels of haematocrit in a blood sample have been accounted for include using an average haematocrit in a calculation or measuring a haematocrit in a separate step and then calculating the concentration of the antigen with respect to the plasma value. These methods, however, are believed to be undesirable, at least because they involve unwanted sample handling, take additional time, and/or lead to substantial errors in the final determinations. Further, temperatures in environments where samples are analyzed can also have a negative impact on the accuracy of analyte concentration determination.

A desirable attribute of all sensor elements is that they have a long shelf life—that is, the sensing characteristic of the sensor element does not change significantly between manufacture and use (i.e. during storage). However, when stored for long periods of time and/or in non-optimal storage conditions, e.g., high temperatures, high humidity, etc., the performance of sensors can degrade. For example, the accuracy of analyte concentration determinations made using such sensors can be reduced. It is an object of the present invention to overcome or ameliorate these and other disadvantages in the prior art.

SUMMARY

Applicants have recognized that it would be desirable to develop a way to obtain more accurate analyte concentration measurements across a wide spectrum of donors, analyte concentration levels, hematocrit levels, temperatures, and sensor storage conditions with little or none of the attendant issues noted previously. Accordingly, systems, devices, and methods are generally provided for determining an accurate concentration of an analyte in a sample. In general the systems, devices and methods disclosed herein include applying a series of corrections to an optimized analyte concentration measurement so as to provide a corrected analyte concentration value of improved accuracy.

In an exemplary embodiment of a method of determining an analyte concentration in a sample, the method includes detecting a sample including an analyte introduced to an electrochemical sensor. The electrochemical sensor can include, for example, two electrodes in a spaced apart configuration. In other embodiments, the two electrodes can include a facing orientation. In other embodiments, the electrochemical sensor can include two electrodes in an opposing faced orientation. In some embodiments, the electrochemical sensor can include a glucose sensor. In other embodiments, the electrochemical sensor can include an immunosensor. In some embodiments, the sample can include blood or whole blood. In some embodiments, the analyte can include C-reactive protein.

The method further includes reacting the analyte to cause a physical transformation of the analyte between the two electrodes. For example, reacting of the analyte can generate an electroactive species that can be measured as a current by the two electrodes. The method also includes measuring current outputs at discrete intervals to derive a fill time of the sample in the sensor and a capacitance of the sensor with the sample. The method also includes determining a first analyte concentration value from the current outputs; calculating a second analyte concentration value from the current outputs and the first analyte concentration value; correcting the second analyte concentration value for temperature effects to provide for a third analyte concentration value; correcting the third analyte concentration value as a function of the fill time of the sensor to provide for a fourth analyte concentration value; and correcting the fourth analyte concentration value as a function of the capacitance to provide for a final analyte concentration value.

In an exemplary embodiment of a method of obtaining increased accuracy of a test strip, the method includes providing for a batch of test strips with each test strip having two electrodes spaced apart with a reagent disposed therebetween. As used herein, the term "batch" refers to a plurality of test strips from the same manufacturing run that are assumed to have similar characteristics. For example, a batch can contain approximately 500 test strips from a manufacturing lot of approximately 180,000 test strips. The method further includes introducing a referential sample containing a referential concentration of an analyte to each of the batch of test strips. The method also includes reacting the analyte to cause a physical transformation of the analyte between the two electrodes; measuring current outputs at discrete intervals to derive a fill time of the sample into the sensor and a capacitance of the sensor with the sample; and determining a first analyte concentration value from the current outputs. The method also includes calculating a second analyte concentration value from the current outputs and the first analyte concentration; correcting the second analyte concentration value for temperature effects to provide for a third analyte concentration value; correcting the third analyte concentration value as a function of the fill time of the sensor to provide for a fourth analyte concentration value; and correcting the fourth analyte concentration value as a function of the capacitance to provide for a final analyte concentration value for each of the batch of test strips such that at least 95% of the final analyte concentration values of the batch of test strips are within 10% of the referential analyte concentration.

In an exemplary embodiment of the aforementioned methods, the current outputs measured at discrete intervals can include a first current summation $i_r$ and a second current summation $i_l$. In some embodiments, the discrete intervals over which the first current summation $i_r$ and a second current summation $i_l$ are measured can be measured from the time a sample is deposited in the test chamber and can include a first interval from about 3.9 seconds to about 4 seconds and a second interval from about 4.25 seconds to about 5 seconds. For example, the first current summation $i_r$ can be expressed by the equation $$i_r = \sum_{t=4.25}^{5} i(t)$$

and the second current summation $i_l$ can be expressed by the equation $$i_l = \sum_{t=3.9}^{4} i(t)$$

where i(t) can include the absolute value of the current measured at time t.

In some exemplary embodiments of the aforementioned methods, the step of determining the first analyte concentration value can include calculating an analyte concentration G1 with an equation of the form:

$$G1 = \left(\frac{i_r}{i_l}\right)^p \{ai_2 - zgr\}$$

where p can be about 0.5246; a can be about 0.03422; $i_2$ can be an antioxidant-corrected current value; and zgr can be about 2.25.

In some exemplary embodiments of the aforementioned methods, the step of calculating the second analyte concentration value can include calculating an analyte concentration G2 with an equation of the form:

$$G2 = \left(\frac{i_r}{i_l} - AFO\right)^{\{p+kG1\}} \{ai_2 - zgr\}$$

where p comprises about 0.5246; a comprises about 0.03422; $i_2$ comprises an antioxidant-corrected current value; AFO comprises about 2.88; zgr comprises about 2.25; and k comprises about 0.0000124.

In some exemplary embodiments of the aforementioned methods, the third analyte concentration value can include a first temperature correction to the second analyte concentration value whenever an ambient temperature is greater than first temperature threshold and a second temperature correction whenever the ambient temperature is less than or equal to the first temperature threshold.

In some exemplary embodiments of the aforementioned methods, the step of correcting the third analyte concentration value as a function of the fill time of the sensor can include calculating a fill time correction factor based on the fill time. For example, the fill time correction factor can be about zero when the fill time is less than a first fill time threshold. For another example, the fill time correction factor can be calculated based on the fill time when the fill time is greater than the first fill time threshold and less than a second fill time threshold. For yet another example, the fill time correction factor can include a constant value when the fill time is greater than the second fill time threshold. In some embodiments, the first fill time threshold can be about 0.2 second and the second fill time threshold can be about 0.4 second.

In some exemplary embodiments of the aforementioned methods, the fourth analyte concentration value can equal the third analyte concentration value when the third analyte concentration value is less than an analyte concentration threshold of, for example, about 100 mg/dL. When the third analyte concentration value is greater than about 100 mg/dL, for example, the fourth analyte concentration value can include a product of the third analyte concentration value, with an offset to the fill time correction factor.

In some exemplary embodiments of the aforementioned methods, the final analyte concentration value can be set to be about equal to the fourth analyte concentration value when the fourth analyte concentration value is less than a first concentration threshold. For example, the first concentration threshold can be about 100 mg/dL. In further exemplary embodiments of the aforementioned methods the final analyte concentration value can include a product of a capacitance correction factor and the fourth analyte concentration value when the fourth analyte concentration value is greater than the first concentration threshold. For example, the capacitance correction factor for the final analyte concentration value can be based on a measured capacitance when the capacitance is less than a first capacitance threshold and the capacitance correction factor can be set to a maximum value when the calculated capacitance correction factor is greater than a set value.

In an exemplary embodiment of an analyte measurement device, the device can include a housing, a strip port connector mounted on the housing and configured to receive an analyte test strip, and a microprocessor disposed in the housing, the microprocessor being connected to the strip port connector, a power supply and a memory such that when an analyte test strip is coupled to the strip port with a sample deposited in a test chamber of the test strip, the analyte is caused to react between the two electrodes and provide for one or more of a first analyte concentration estimate G1 based on measured output current values over discrete intervals during a reaction of the analyte, a second analyte concentration estimate G2 based on measured output current values over discrete intervals during a reaction of the analyte, a temperature corrected analyte concentration value G3 from the second analyte concentration value G2, a sample fill time corrected analyte concentration value G4 from the third analyte concentration G3, and a test strip capacitance corrected final concentration value G5 from the sample fill-time corrected analyte concentration value G4.

In an exemplary embodiment of an analyte measurement system, the system can include a plurality of test strips, each test strip having at least two electrodes spaced apart in a test chamber and a reagent disposed therebetween to receive a sample containing an analyte. The system can also include an analyte measurement device. The analyte measurement device can include a strip port having connectors configured to mate with respective electrodes of each test strip and a microprocessor coupled to the strip port. The microprocessor can be configured to measure current, test strip capacitance, and sample fill time with the electrodes of each test strip when a referential sample is deposited in the test chamber of each of the plurality of test strips and a final analyte concentration determined based on the current, sample fill time, and the test strip capacitance so that a percentage of the final analyte concentration values from the batch of test strips are within 10% of a referential analyte value above a threshold analyte value.

In some embodiments, the microprocessor can be configured so that when an analyte test strip of the plurality of test strips is coupled to the strip port with a sample deposited therein, an analyte in the sample reacts between the two electrodes to provide for a first analyte concentration estimate G1 based on measured output current values over discrete intervals, second analyte concentration estimate G2 based on measured output current values over discrete intervals, temperature corrected analyte concentration value G3 from the second analyte concentration value G2, sample fill time corrected analyte concentration value G4 from the third analyte concentration, and test strip capacitance corrected final concentration value G5 from the sample fill-time corrected analyte concentration value G4.

In an exemplary embodiment, the discrete intervals can be measured from the time a sample is deposited in the test chamber and can include a first interval from about 3.9 seconds to about 4 seconds and a second interval from about 4.25 seconds to about 5 seconds. The output current values measured over the first and second intervals can include a first current summation $i_r$ and a second current summation $i_l$, where $$i_r = \sum_{t=4.25}^{5} i(t)$$

and $$i_l = \sum_{t=3.9}^{4} i(t)$$

where i(t) comprises the absolute value of the current measured at time t.

In some embodiments, the first analyte concentration value G1 can include derivation of the current values with an equation of the form:

$$G1 = \left(\frac{i_r}{i_l}\right)^p \{ai_2 - zgr\}$$

where p comprises about 0.5246; a comprises about 0.03422; $i_2$ comprises an antioxidant-corrected current value; and zgr comprises about 2.25.

In some embodiments, the second analyte concentration value G2 can include derivation with an equation of the form:

$$G2 = \left(\frac{i_r}{i_l} - AFO\right)^{\{p+kG1\}} \{ai_2 - zgr\}$$

where p comprises about 0.5246; a comprises about 0.03422; $i_2$ comprises an antioxidant-corrected current value; AFO comprises about 2.88; zgr comprises about 2.25; and k comprises about 0.0000124.

In some embodiments, the antioxidant current value $i_2$ can include an equation of the form:

$$i_2 = i_r\left(\frac{i(4.1) - 2i(1.1) + i_{ss}}{i(4.1) + i_{ss}}\right)$$

where i(4.1) comprises an absolute value of the current during a third electric potential; i(1.1) comprises an absolute value of the current during a second electric potential; and $i_{ss}$ comprises a steady-state current.

In some embodiments, $i_{ss}$ can include an equation of the form:

$$i_{ss} = \frac{i(5)}{1 + 4e^{-4\pi^2 D/L^2}}$$

where i(5) comprises an absolute value of the current during a third electric potential; π comprises a constant; D comprises a diffusion coefficient of a redox species, and L comprises a distance between the two electrodes.

In some embodiments, the temperature corrected analyte concentration value G3 can be corrected by a fill time correction factor based on a fill time. For example, the fill time correction factor can be about zero when the fill time is less than a first fill time threshold. For another example, when the fill time is greater than the first fill time threshold and less than a second fill time threshold, the fill time correction factor can be calculated based on the fill time. For yet another example, when the fill time is greater than the second fill time threshold, the fill time correction factor can include a constant value. In some embodiments, the first fill time threshold can be about 0.2 second and the second fill time threshold can be about 0.4 second.

In some embodiments, the temperature corrected analyte concentration value G3 can include a first temperature correction to the second analyte concentration value G2 whenever an ambient temperature is greater than first temperature threshold and a second temperature correction whenever the ambient temperature is less than or equal to the first temperature threshold.

In some embodiments, the fill time corrected analyte concentration value G4 can be the temperature corrected concentration value G3 when the temperature corrected concentration value G3 is less than a concentration threshold of, for example, about 100 mg/dL and the fill time corrected concentration value G4 can include a percentage increase in the third analyte concentration value in view of the fill time correction factor when the temperature corrected concentration value G3 is greater than a concentration threshold of, for example, about 100 mg/dL.

In some embodiments, the test strip capacitance corrected final concentration value G5 can be set to equal to the fourth analyte concentration value when the sample fill-time corrected analyte concentration value G4 is less than a first concentration threshold. For example, the first concentration threshold can be about 100 mg/dL. In some embodiments, the test strip capacitance corrected final concentration value G5 can include a product of a capacitance correction factor and the sample fill-time corrected analyte concentration value G4 when the sample fill-time corrected analyte concentration value G4 is greater than the first concentration threshold. For example, the capacitance correction factor for the final analyte concentration value G5 can be based on a measured capacitance when the capacitance is less than the first capacitance threshold and the capacitance correction factor can be set to a maximum value when the calculated capacitance correction factor is greater than a set value.

In another embodiment of an exemplary method for determining a concentration of an analyte in a sample, the method includes introducing a sample including an analyte to an electrochemical sensor. The method further includes reacting the analyte to cause a physical transformation of the analyte between the two electrodes and determining a concentration of the analyte.

In another exemplary method of a method for measuring a corrected analyte concentration in a sample, the method includes detecting a presence of the sample in an electrochemical sensor. The electrochemical sensor can include two electrodes. The method also includes reacting an analyte to cause a physical transformation of the analyte, determining a first analyte concentration in the sample, and calculating a corrected analyte concentration based on the first analyte concentration and one or more correction factors.

In some embodiments, the step of determining a concentration of the analyte can include a step of correcting for one or more of a fill time of the sample, a physical property of the electrochemical cell, a temperature of the sample, a temperature of the electrochemical sensor, and glucose reaction kinetics. In exemplary embodiments, the step of correcting for glucose reaction kinetics can include calculating a first analyte concentration and calculating a second analyte concentration that depends on the first analyte concentration, such that the magnitude of the correction for glucose reaction kinetics is proportional to the magnitude of the first analyte concentration.

In some embodiments, the physical property of the electrochemical sensor can be related to at least one of an age of the electrochemical sensor and a storage condition of the electrochemical sensor. For example, the physical property can be a capacitance of the electrochemical cell.

In an exemplary embodiment of an electrochemical system, the system includes an electrochemical sensor including electrical contacts configured to mate with a test meter. The electrochemical sensor can include a first electrode and a second electrode in a spaced apart relationship and a reagent. The test meter can include a processor configured to receive current data from the electrochemical sensor upon application of voltages to the test strip. The test meter can be further configured to determine a corrected analyte concentration based on a calculated analyte concentration and one or more of a fill time of the sample, a physical property of the electrochemical sensor, a temperature of the sample, a temperature of the electrochemical sensor, and glucose reaction kinetics.

In some embodiments, the test meter can include data storage containing an analyte concentration threshold and a plurality of thresholds related to one or more of a fill time of the sample, a physical property of the electrochemical sensor, a temperature of the sample, a temperature of the electrochemical sensor, and glucose reaction kinetics.

In some embodiments, the electrochemical system can include a heating element configured to heat at least a portion of the electrochemical sensor. In some embodiments, at least one of the electrochemical sensor, the test meter, and the processor can be configured to measure a temperature of the sample.

In some embodiments, the systems and methods can reduce variation in analyte concentration determinations from, for example, donor-to-donor and/or gender-to-gender. The method can also reduce interference by urate concentration on the determination of analyte concentration.

In some embodiments, the systems and methods of the present invention can achieve an accuracy standard of at least ±10% for certain analyte (e.g., glucose) concentrations above an analyte concentration threshold, such that at least 95% of a series of analyte concentration evaluations yield an analyte concentration value that is accurate to within 10% of a reference analyte measurement. In another exemplary embodiment, the method can achieve an accuracy standard of at least ±10 mg/dL for analyte concentrations (e.g., plasma glucose in a whole blood sample) below the analyte concentration threshold, such that at least 95% of a series of analyte concentration evaluations yield an analyte concentration value that is accurate to within about 10 mg/dL of a reference analyte measurement. For example, the analyte concentration threshold can be about 75 mg/dL of plasma glucose in a whole blood sample.

For another example, the accuracy standard can achieved over a series of more than about 5,000 analyte concentration evaluations. For yet another example, the accuracy standard can be achieved over a series of more than about 18,000 analyte concentration evaluations.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

Various features of the present disclosure are set forth with particularity in the appended claims. A better understanding of such features can be obtained by reference to the following detailed description that sets forth illustrative, non-limiting embodiments and the accompanying drawings of which:

DETAILED DESCRIPTION

Figure 1A:
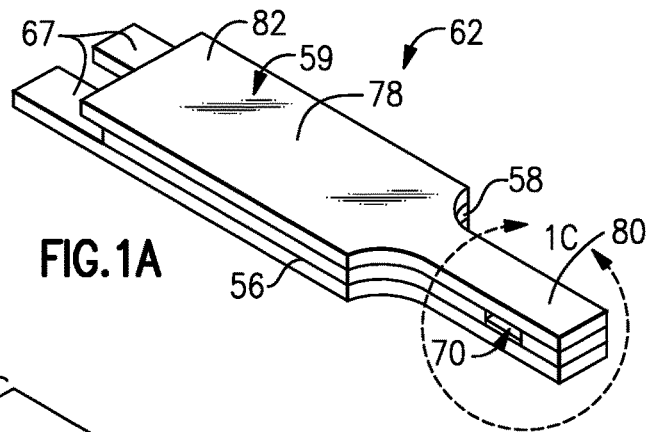
FIG. 1A illustrates a perspective view of an exemplary test strip.
Figure 1B:
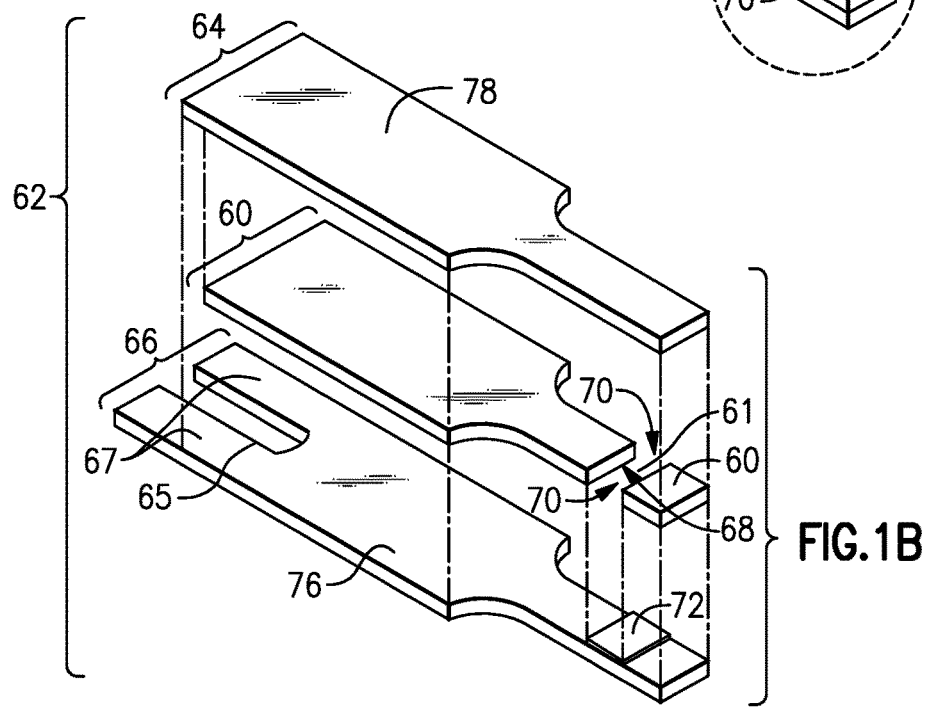
FIG. 1B illustrates an exploded perspective view of the test strip of FIG. 1A.
Figure 1C:
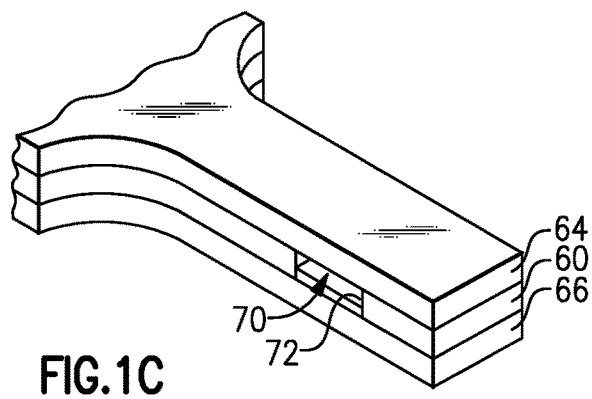
FIG. 1C illustrates a perspective view of a distal portion of the test strip of FIG. 1A.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

As will be discussed in more detail below, the disclosed systems and methods include determining a first analyte concentration value; calculating a second analyte concentration value from the first analyte concentration value; correcting the second analyte concentration value for temperature effects to provide for a third analyte concentration value; correcting the third analyte concentration value as a function of the fill time of the sensor to provide for a fourth analyte concentration value; and correcting the fourth analyte concentration value as a function of the capacitance to provide for a final analyte concentration value.

The presently disclosed systems and methods are suitable for use in the determination of a wide variety of analytes in a wide variety of samples, and are particularly suited for use in the determination of analytes in whole blood, plasma, serum, interstitial fluid, or derivatives thereof. In an exemplary embodiment, a glucose test system based on a thin-layer cell design with opposing electrodes and tri-pulse electrochemical detection that is fast (e.g., about 5 second or less analysis time), requires a small sample (e.g., about 0.4 µL or less), and can provide improved reliability and accuracy of blood glucose measurements. In the reaction cell to assay analyte, glucose in the sample can be oxidized to gluconolactone using glucose dehydrogenase and an electrochemically active mediator can be used to shuttle electrons from the enzyme to a working electrode. More particularly, a reagent layer coating at least one of the electrodes in the reaction cell can include glucose dehydrogenase (GDH) based on pyrroloquinoline quinone (PQQ) co-factor and ferricyanide. In another embodiment, the enzyme GDH based on the PQQ co-factor may be replaced with the enzyme GDH based on the flavin adenine dinucleotide (FAD) co-factor. When blood or control solution is dosed into the reaction chamber, glucose is oxidized by GDH(ox) and in the process converts GDH(ox) to GDH(red), as shown in the chemical transformation T.1 below. Note that GDH(ox) refers to the oxidized state of GDH, and GDH (red) refers to the reduced state of GDH.

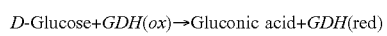

$$D\text{-Glucose} + GDH(ox) \rightarrow \text{Gluconic acid} + GDH(red) \qquad \text{T.1}$$

A potentiostat can be utilized to apply a tri-pulse potential waveform to the working and counter electrodes, resulting in test current transients used to calculate the glucose concentration. Further, additional information gained from the test current transients may be used to discriminate between sample matrices and correct for variability in blood samples due to hematocrit, temperature variation, electrochemically active components, and identify possible system errors.

The subject methods can be used, in principle, with any type of electrochemical cell sensor having spaced apart first and second electrodes and a reagent layer. For example, an electrochemical cell sensor can be in the form of a test strip. In one aspect, the test strip may include two opposing electrodes separated by a thin spacer for defining a sample-receiving chamber or zone in which a reagent layer is located. Applicants note that other types of test strips, including, for example, test strips with co-planar electrodes may also be used with the systems and methods described herein. The devices used with the systems and methods described herein typically include at least one working electrode and one counter electrode between which an electric potential can be applied. The sample analyzing device can generally be associated with a component for applying the electric potential between the electrodes, such as a meter. Applicants note that a variety of test meters can be used with the systems and methods described herein. However, in one embodiment, the test meter includes at least a processor, which may include one or more control units configured for performing calculations capable of calculating a correction factor in view of at least one measured or calculated parameter as well as configured for data sorting and/or storage. The microprocessor can be in the form of a mixed signal microprocessor (MSP) such as, for example, the Texas Instruments MSP 430. The TI-MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit.

Electrochemical Cells

FIGS. 1A-4B show various views of an exemplary test strip 62 suitable for use with the methods described herein. As shown, the test strip 62 can include an elongate body extending from a distal end 80 to a proximal end 82, and having lateral edges 56, 58. The distal portion of the body 59 can include a sample reaction chamber 61 having multiple electrodes 64, 66 and a reagent 72, while the proximal portion of the test strip body 59 can include features configured for electrically communicating with a test meter. In use, physiological fluid or a control solution can be delivered to the sample reaction chamber 61 for electrochemical analysis. As used herein, the term "proximal" indicates that a reference structure is closer to the test meter and the term "distal" indicates that a reference structure is further away from the test meter.

In the illustrative embodiment, the test strip 62 can include a first electrode layer 66 and a second electrode layer 64, with a spacer layer 60 positioned therebetween. The first electrode layer 66 can provide a first electrode 166 and a first connection track 76 for electrically connecting the first electrode 166 to a first electrical contact 67. Similarly, the second electrode layer 64 can provide a second electrode 164 and a second connection track 78 for electrically connecting the second electrode 164 with a second electrical contact 63.

In one embodiment, the sample reaction chamber 61 is defined by the first electrode 166, the second electrode 164, and a spacer 60 as shown in FIGS. 1A-4B. Specifically, the first electrode 166 and the second electrode 164 define, respectively, the bottom and top of the sample reaction chamber 61. A cutout area 68 of the spacer 60 can define the side walls of the sample reaction chamber 61. In one aspect, the sample reaction chamber 61 can further include a number of ports 70 that provide a sample inlet and/or a vent. For example, one of the ports can provide a fluid sample ingress and the other port can act as a vent.

The sample reaction chamber 61 can have a small volume. For example, the volume can range from about 0.1 microliters to about 5 microliters, preferably about 0.2 microliters to about 3 microliters, and more preferably about 0.3 microliters to about 1 microliter. As will be appreciated by those skilled in the art, the sample reaction chamber 61 can have various other such volumes. To provide the small sample volume, the cutout 68 can have an area ranging from about 0.01 cm$^2$ to about 0.2 cm$^2$, preferably about 0.02 cm$^2$ to about 0.15 cm$^2$, and more preferably about 0.03 cm$^2$ to about 0.08 cm$^2$. Similarly, those skilled in the art will appreciate that the volume cutout 68 can be of various other such areas. In addition, the first and second electrode 166, 164 can be spaced in the range of about 1 micron to about 500 microns, preferably in the range of about 10 microns to about 400 microns, and more preferably in the range of about 40 microns to about 200 microns. In other embodiments, such a range can vary between various other values. The close spacing of the electrodes can also allow redox cycling to occur, where oxidized mediator generated at the first electrode 166, can diffuse to the second electrode 164 to become reduced, and subsequently diffuse back to the first electrode 166 to become oxidized again.

Figure 2:
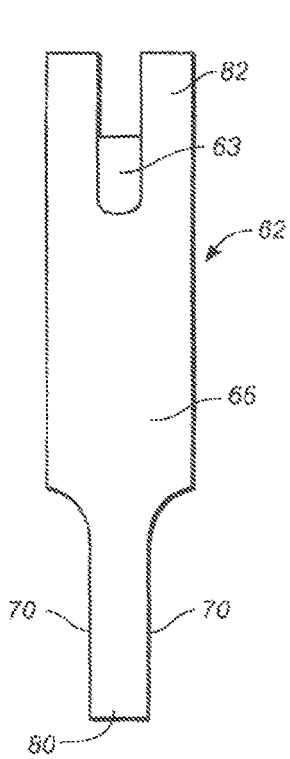
FIG. 2 illustrates a bottom plan view of the test strip of FIG. 1A.
Figure 3:
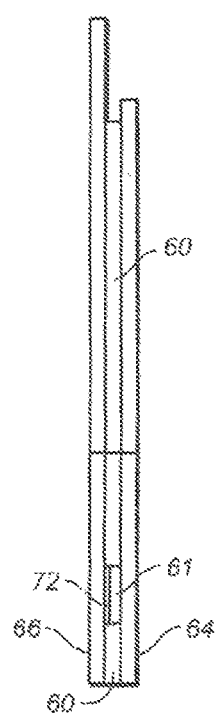
FIG. 3 illustrates a side plan view of the test strip of FIG. 1A.

At the proximal end of the test strip body 59, a first electrical contact 67 can be used to establish an electrical connection to a test meter. A second electrical contact 63 can be accessed by the test meter through a U-shaped notch 65 as illustrated in FIG. 2. Applicants note that the test strip 62 can include a variety of alternative electrical contacts configured for electrically connecting to a test meter. For example, U.S. Pat. No. 6,379,513, the entirety of which is hereby incorporated herein by reference, discloses an electrochemical cell connection means.

In one embodiment, the first electrode layer 66 and/or the second electrode layer 64 can be a conductive material formed from materials such as gold, palladium, carbon, silver, platinum, tin oxide, iridium, indium, and combinations thereof (e.g., indium doped tin oxide). In addition, the electrodes can be formed by disposing a conductive material onto an insulating sheet (not shown) by various processes such as, for example, a sputtering, electroless plating, or a screen printing process. In one exemplary embodiment, the second electrode layer 64 can be a sputtered gold electrode and the first electrode layer 66 can be a sputtered palladium electrode. Suitable materials that can be employed as the spacing layer 60 include various insulating materials, such as, for example, plastics (e.g., PET, PETG, polyimide, polycarbonate, polystyrene), silicon, ceramic, glass, adhesives, and combinations thereof.

A reagent layer 72 can be disposed within the sample reaction chamber 61 using a process such as slot coating, dispensing from the end of a tube, ink jetting, and screen printing. Such processes are described, for example, in the following U.S. Pat. Nos. 6,749,887; 6,869,411; 6,676,995; and 6,830,934, the entirety of each of these references being incorporated herein by reference. In one embodiment, the reagent layer 72 can include at least a mediator and an enzyme, and can be deposited onto the first electrode 166.

Various mediators and/or enzymes are within the spirit and scope of the present disclosure. For example, suitable mediators include ferricyanide, ferrocene, ferrocene derivatives, osmium bipyridyl complexes, and quinone derivatives. Examples of suitable enzymes include glucose oxidase, glucose dehydrogenase (GDH) based on pyrroloquinoline quinone (PQQ) co-factor, GDH based on nicotinamide adenine dinucleotide co-factor, and FAD-based GDH [E.C.1.1.99.10]. One exemplary reagent formulation, which would be suitable for making the reagent layer 72, is described in pending U.S. application Ser. No. 10/242,951, entitled, "Method of Manufacturing a Sterilized and Calibrated Biosensor-Based Medical Device", published as U.S. Published Patent Application No. 2004/0120848, the entirety of which is hereby incorporated herein by reference.

Either the first electrode 166 or the second electrode 164 can function as working electrode which oxidizes or reduces a limiting amount of mediator depending on the polarity of the applied test potential of the test meter. For example, if the current limiting species is a reduced mediator, it can be oxidized at the first electrode 166 as long as a sufficiently positive potential was applied with respect to the second electrode 164. In such a situation, the first electrode 166 performs the function of the working electrode and second electrode 164 performs the function of a counter/reference electrode. It should be noted that unless otherwise stated for test strip 62, all potentials applied by test meter 100 will hereinafter be stated with respect to second electrode 164.

Similarly, if a sufficiently negative potential is applied with respect to the second electrode 164, then the reduced mediator can be oxidized at the second electrode 164. In such a situation, the second electrode 164 can perform the function of the working electrode and the first electrode 166 can perform the function of the counter/reference electrode.

Initially, the presently disclosed method can include introducing a quantity of the fluid sample of interest into the test strip 62, which includes the first electrode 166, the second electrode 164 and a reagent layer 72. The fluid sample can be whole blood or a derivative or fraction thereof, or a control solution. The fluid sample, e.g., blood, can be dosed into the sample reaction chamber 61 via the port 70. In one aspect, the port 70 and/or the sample reaction chamber 61 can be configured such that capillary action causes the fluid sample to fill the sample reaction chamber 61.

Figure 5A:
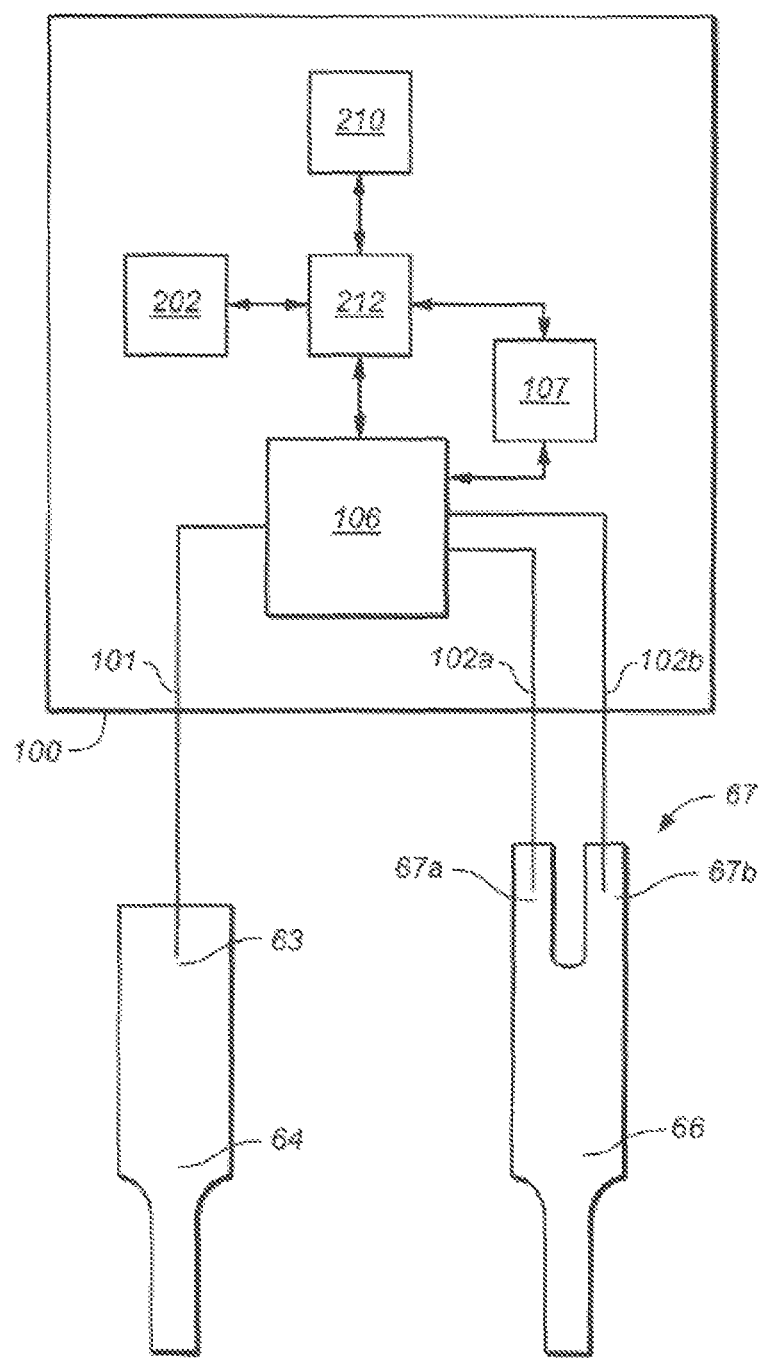
FIG. 5A illustrates a simplified schematic showing a test meter electrically interfacing with the test strip contact pads.

FIG. 5A provides a simplified schematic of a test meter 100 interfacing with a first electrical contact 67 and a second electrical contact 63, which are in electrical communication with the first electrode 166 and the second electrode 164, respectively, of the test strip 62. The test meter 100 can be configured to electrically connect to the first electrode 166 and the second electrode 164 via a first electrical contact 67 and a second electrical contact 63, respectively (as shown in FIGS. 2 and 5A). As will be appreciated by those skilled in the art, a variety of test meters can be used with the method described herein. However, in one embodiment, the test meter includes at least a processor, which may include one or more control units configured for performing calculations capable of calculating a correction factor in view of at least one measured parameter correlating to a physical property of the electrochemical cell, as well as configured for data sorting and/or storage. The microprocessor can be in the form of a mixed signal microprocessor (MSP) such as, for example, the Texas Instruments MSP 430. The TI-MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit.

As illustrated in FIG. 5A, an electrical contact 67 can include two prongs 67a, 67b. In one exemplary embodiment, the test meter 100 separately connects to the prongs 67a, 67b, such that when the test meter 100 interfaces with a test strip 62 a circuit is completed. The test meter 100 can measure the resistance or electrical continuity between the prongs 67a, 67b to determine whether the test strip 62 is electrically connected to the test meter 100. Applicants note that the test meter 100 can use a variety of sensors and circuits to determine when the test strip 62 is properly positioned with respect to the test meter 100.

In one embodiment, a circuit disposed in the test meter 100 can apply a test potential and/or a current between first electrical contact 67 and second electrical contact 63. Once test meter 100 recognizes that strip 62 has been inserted, test meter 100 turns on and initiates a fluid detection mode. In one embodiment, the fluid detection mode causes test meter 100 to apply a constant current of about 1 microampere between first electrode 166 and second electrode 164. Because test strip 62 is initially dry, test meter 100 measures a maximum voltage, which is limited by the hardware within test meter 100. However, once a user doses a fluid sample onto inlet 70, this causes sample reaction chamber 61 to become filled. When the fluid sample bridges the gap between first electrode 166 and second electrode 164, test meter 100 will measure a decrease in measured voltage (e.g., as described in U.S. Pat. No. 6,193,873, the entirety of which being incorporated herein by reference), which is below a predetermined threshold causing test meter 100 to automatically initiate the glucose test.

It should be noted that the measured voltage may decrease below a pre-determined threshold when only a fraction of the sample reaction chamber 61 has been filled. A method of automatically recognizing that a fluid was applied does not necessarily indicate that the sample reaction chamber 61 has been completely filled, but can only confirm a presence of some amount of fluid in the sample reaction chamber 61. Once the test meter 100 determines that a fluid has been applied to test strip 62, a short, but non-zero amount of time may still be required to allow the fluid to completely fill the sample reaction chamber 61.

Figure 5B:
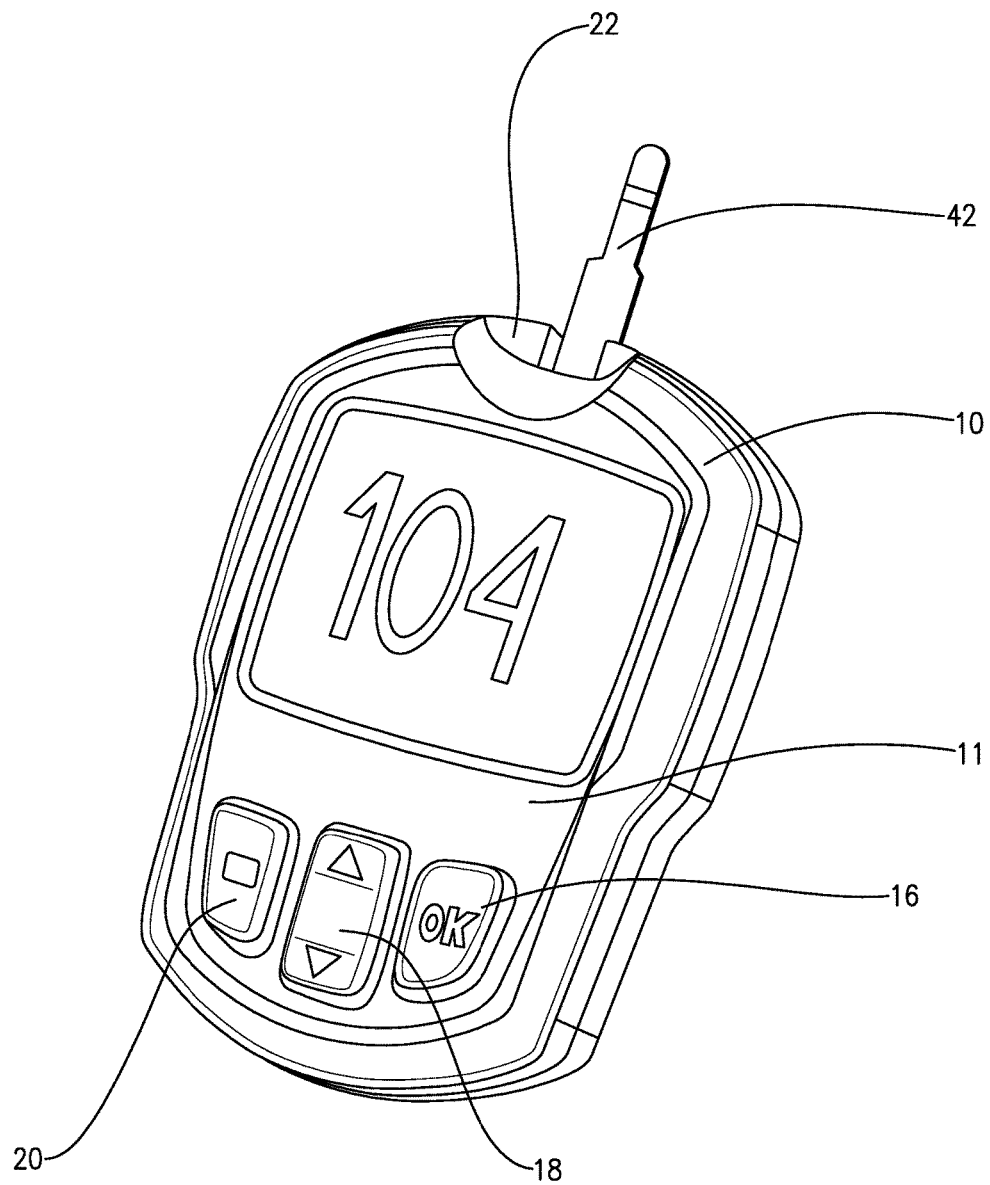
FIG. 5B illustrates an exemplary analyte measurement system including an analyte test meter and test strip.

FIG. 5B illustrates a diabetes management system that includes a diabetes data management unit 10 and a biosensor in the form of a glucose test strip 42. Note that the diabetes data management unit (DMU) may be referred to as an analyte measurement and management unit, a glucose meter, a meter, and an analyte measurement device. In an embodiment, the DMU may be combined with an insulin delivery device, an additional analyte testing device, and a drug delivery device. The DMU may be connected to a computer or server via a cable or a suitable wireless technology such as, for example, GSM, CDMA, BlueTooth, WiFi and the like.

Referring back to FIG. 5B, the DMU 10 can include a housing 11, user interface buttons (16, 18, and 20), a display 14, and a strip port opening 22. User interface buttons (16, 18, and 20) can be configured to allow the entry of data, navigation of menus, and execution of commands. User interface button 18 can be in the form of a two way toggle switch. Data can include values representative of analyte concentration, and/or information, which are related to the everyday lifestyle of an individual. Information, which is related to the everyday lifestyle, can include food intake, medication use, occurrence of health check-ups, and general health condition and exercise levels of an individual.

Figure 5C:
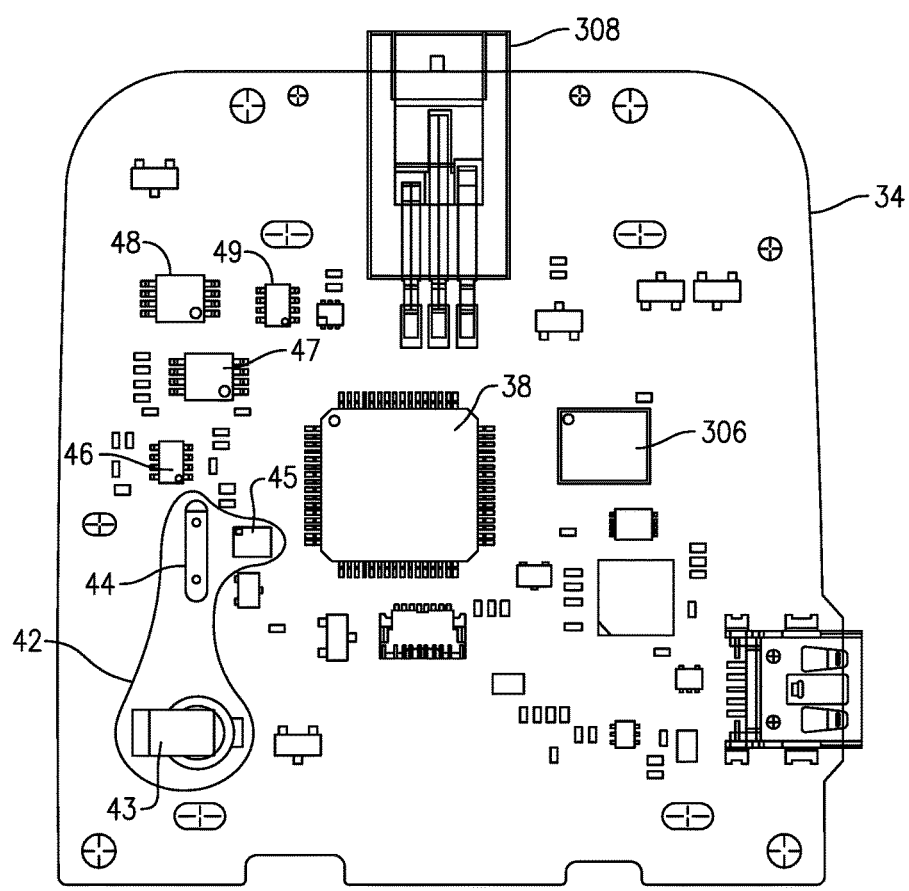
FIG. 5C illustrates a simplified schematic view of an exemplary circuit board for the meter of FIG. 5B.

The electronic components of DMU 10 can be disposed on a circuit board 34 that is within housing 11. FIG. 5C illustrates (in simplified schematic form) the electronic components disposed on a top surface of circuit board 34. On the top surface, the electronic components may include a strip port opening 308, a microcontroller 38, a non-volatile flash memory 306, a data port 13, a real time clock 42, and a plurality of operational amplifiers (46-49). On the bottom surface, the electronic components may include a plurality of analog switches, a backlight driver, and an electrically erasable programmable read-only memory (EEPROM, not shown). Microcontroller 38 can be electrically connected to strip port opening 308, non-volatile flash memory 306, data port 13, real time clock 42, the plurality of operational amplifiers (46-49), the plurality of analog switches, the backlight driver, and the EEPROM.

Referring back to FIG. 5C, the plurality of operational amplifiers can include gain stage operational amplifiers (46 and 47), a trans-impedance operational amplifier 48, and a bias driver operational amplifier 49. The plurality of operational amplifiers can be configured to provide a portion of the potentiostat function and the current measurement function. The potentiostat function can refer to the application of a test voltage between at least two electrodes of a test strip. The current function can refer to the measurement of a test current resulting from the applied test voltage. The current measurement may be performed with a current-to-voltage converter. Microcontroller 38 can be in the form of a mixed signal microprocessor (MSP) such as, for example, the Texas Instruments MSP 430. The MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit (ASIC).

Strip port connector 308 can be located proximate the strip port opening 22 and configured to form an electrical connection to the test strip. Display 14 can be in the form of a liquid crystal display for reporting measured glucose levels, and for facilitating entry of lifestyle related information. Display 14 can optionally include a backlight. Data port 13 can accept a suitable connector attached to a connecting lead, thereby allowing glucose meter 10 to be linked to an external device such as a personal computer. Data port 13 can be any port that allows for transmission of data such as, for example, a serial, USB, or a parallel port.

Real time clock 42 can be configured to keep current time related to the geographic region in which the user is located and also for measuring time. Real time clock 42 may include a clock circuit 45, a crystal 44, and a super capacitor 43. The DMU can be configured to be electrically connected to a power supply such as, for example, a battery. The super capacitor 43 can be configured to provide power for a prolonged period of time to power real time clock 42 in case there is an interruption in the power supply. Thus, when a battery discharges or is replaced, real time clock does not have to be re-set by the user to a proper time. The use of real time clock 42 with super capacitor 43 can mitigate the risk that a user may re-set real time clock 42 incorrectly.

Figure 6:
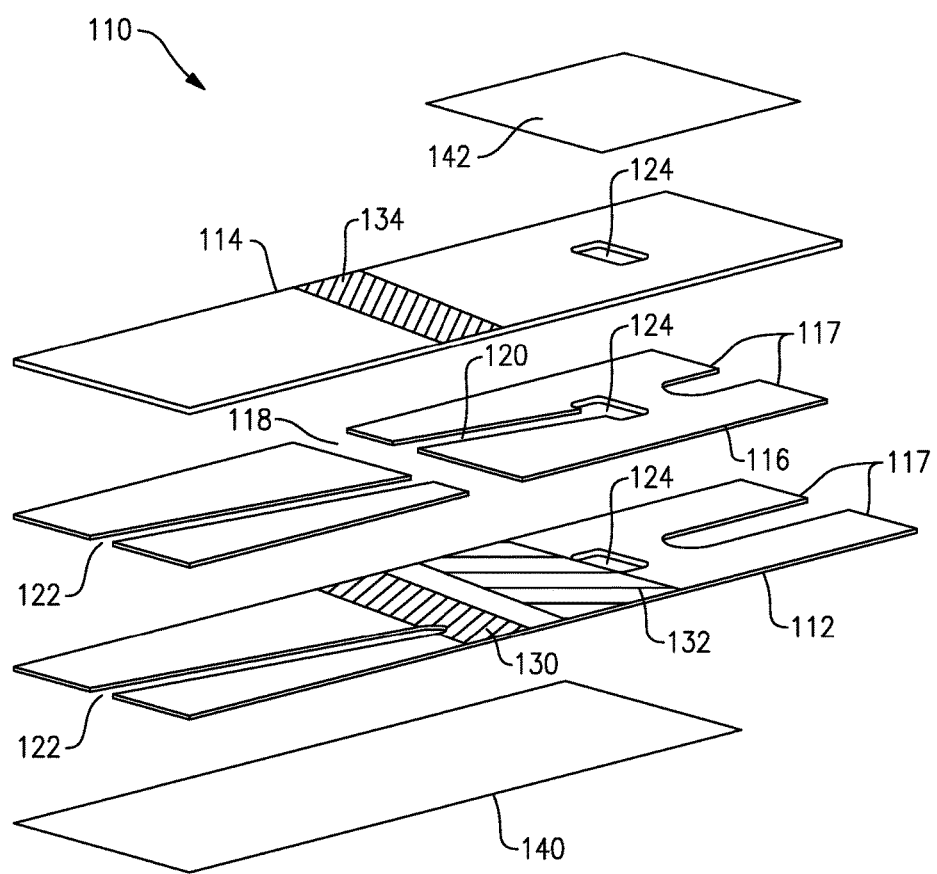
FIG. 6 illustrates an exploded view of an exemplary embodiment of an immunosensor.

Another exemplary embodiment of a sample analyzing device for use in conjunction with at least some of the methods disclosed herein, an immunosensor 110, is illustrated in FIG. 6 and is described in U.S. patent application Ser. No. 12/570,268 of Chatelier et al., entitled "Adhesive Compositions for Use in an Immunosensor" and filed on Sep. 30, 2009, the contents of which is hereby incorporated by reference in its entirety. A plurality of chambers can be formed within the immunosensor, including a fill chamber, by which a sample can be introduced into the immunosensor, a reaction chamber, by which a sample can be reacted with one or more desired materials, and a detection chamber, by which a concentration of a particular component of the sample can be determined. These chambers can be formed in at least a portion of a first electrode, a second electrode, and a separator of the immunosensor. The immunosensor can also include a vent hole to allow air to enter and escape the immunosensor as desired, and first and second sealing components to selectively seal first and second sides of the vent hole. The first sealing component can also form a wall of the fill chamber.

As illustrated, the immunosensor 110 includes a first electrode 112 having two liquid reagents 130, 132 striped onto it. The first electrode 112 can be formed using any number of techniques used to form electrodes, but in one embodiment a polyethylene terephthalate (PET) sheet that is filled with barium sulphate is sputter-coated with gold. The PET sheet can also be filled with titanium dioxide. Other non-limiting example of forming an electrode are disclosed in U.S. Pat. No. 6,521,110 of Hodges et al., entitled "Electrochemical Cell" and filed on Nov. 10, 2000, the contents of which is hereby incorporated by reference in its entirety.

Likewise, the liquid reagents 130, 132 can have a number of different compositions. In one embodiment the first liquid reagent 130 includes an antibody conjugated to an enzyme, such as GDH-PQQ, in a buffer that contains sucrose, as well as a poloxamer, such as Pluronics® block copolymers, an anticoagulant, such as citraconate, and calcium ions. In one embodiment the second liquid reagent 132 includes a mixture of ferricyanide, glucose, and a second mediator, such as phenazine ethosulfate, in an acidic buffer, such as a dilute citraconic acid solution. The first and second liquid reagents 130, 132 can be dried onto the first electrode 112. A number of techniques can be used to dry the reagents 130, 132, but in one embodiment, following the striping of the reagents 130, 132 on the first electrode 112, one or more infrared dryers can be applied to the reagents 130, 132. One or more air dryers can also be used, for example, subsequent to the infrared dryers. References to a first reagent and a first liquid reagent and a second reagent and a second liquid reagent herein are used interchangeably and are not necessarily an indication that the reagents are in their liquid or dried form at a given time for a particular embodiment. Further, some of the components associated with the first and second liquid reagents can be used interchangeably and/or in both the first and second liquid reagents as desired. By way of non-limiting example, an anticoagulant can be associated with either or both of the first liquid reagent 130 and the second liquid reagent 132.

An electrically insulating line can be formed in the sputter-coated gold between the reagents 130, 132 such that an edge of reagent 132 is very close to, or touches, the line. The line can be applied using laser ablation or with a sharp metal edge. In one exemplary embodiment the line can be applied before the reagents 130, 132 are striped on the electrode. The line can be designed to electrically insulate the section of the first electrode 112 under the detection chamber from the section that will be under the reaction chamber. This can provide a better definition of an area of the working electrode during the electrochemical assay.

The immunosensor 110 can also include a second electrode 114 having one or more magnetic beads 134 containing surface-bound antigens thereon. The antigens can be configured to react with the antibody disposed on the first electrode 112 and the sample within a reaction chamber 118, as described in further detail below. One skilled in the art will recognize that the components disposed on the first electrode 112 and on the second electrode 114 can be interchangeable. Thus, the first electrode 112 can include one or more magnetic beads 134 and the second electrode 114 can include two liquid reagents 130, 132 striped onto it. Further, although in the illustrated embodiment the length of the electrode 112 forms the length of the entire body of the immunosensor 110, in other embodiments the electrode can be only a portion of a layer of an immunosensor that serves as the first or second electrodes or multiple electrodes can be disposed on a single layer of an immunosensor. Further, because voltage applied to the immunosensor can be flipped and/or alternated, each of the first and second electrodes can serve as the working electrode and the counter or counter/reference electrode at different stages. For ease of description purposes, in the present application the first electrode is considered the working electrode and the second electrode the counter or counter/reference electrode.

A separator 116 disposed between the first and second electrodes 112, 114 can have a variety of shapes and sizes, but it generally is configured to desirably engage the first and second electrodes 112, 114 to form the immunosensor 110. In one exemplary embodiment, the separator 116 includes adhesive on both sides. The separator 116 can further include a release liner on each side of the two sides of the separator 116 in order to facilitate the manufacturing process. Each release liner is removed before the separator is bonded to each electrode. The separator 116 can be cut in a manner that forms at least two cavities. A first cavity can be formed to serve as a reaction chamber 118 and a second cavity can be formed to serve as a detection chamber 120. In one embodiment, the separator 116 can be kiss-cut such that the reaction chamber 118 is aligned with the electrodes 112, 114 to allow an antigen-antibody reaction therein while the detection chamber 120 is aligned with the electrodes 112, 114 to allow for the electrochemical determination of ferrocyanide therein.

In one embodiment, the separator 116 can be placed on the first electrode 112 in a manner that allows the magnetic beads 134 of the second electrode 114 and the first reagent 130 of the first electrode 112 to be at least partially disposed in the reaction chamber 118 and the ferricyanide-glucose combination of the second reagent 132 of the first electrode 112 to be at least partially disposed in the detection chamber 120. It can be advantageous to include an anticoagulant in each of the first and second liquid reagents 130, 132 so that an anticoagulant is associated with each of the reaction and detection chambers 118, 120. In some embodiments the combination of one of the first and second electrodes 112, 114 and the separator 116 can be laminated together to form a bi-laminate, while in other embodiments the combination of each of the first electrode 112, the second electrode 114, and the separator 116 can be laminated together to form a tri-laminate. Alternatively, additional layers may also be added.

A fill chamber 122 can be formed by punching a hole into one of the first and second electrodes 112, 114 and the separator 116. In the illustrated embodiment the fill chamber is formed by punching a hole in the first electrode 112 and the separator 116 such that the hole in the first electrode 112 overlaps the reaction chamber 118. As shown, the fill chamber 122 can be a distance apart from the detection chamber 120. Such a configuration allows a sample to enter the immunosensor 110 through the fill chamber 122 and flow into the reaction chamber 118 to be reacted, for example with the first liquid reagent 130 that includes the antibody conjugated to an enzyme in a buffer on the first electrode 112 and the magnetic beads 134 striped on the second electrode 114, without entering the detection chamber 120. Once the sample has been reacted, it can then flow into the detection chamber 120 to undergo a chemical or physical transformation with the second liquid reagent 132, for example the mixture of ferricyanide, glucose, and the second mediator in an acidic buffer.

A vent 124 can be formed by punching a hole through each of the two electrodes 112, 114 and the separator 116 such that the vent 124 extends through the entirety of the immunosensor 110. The hole can be formed in a suitable manner, such as, for example, drilled or punched in a number of different locations, but in one exemplary embodiment it can overlap a region of the detection chamber 120 that is spaced apart from the reaction chamber 118.

The vent 124 can be sealed in a number of different manners. In the illustrated embodiment, a first sealing component 140 is located on the first electrode 112 to seal a first side of the vent 124 and a second sealing component 142 is located on the second electrode 114 to seal a second side of the vent 124. The sealing components can be made of and/or include any number of materials. By way of non-limiting example, either or both of the sealing components can be hydrophilic adhesive tape or Scotch® tape. Adhesive sides of the sealing components can face the immunosensor 110. As shown, not only can the first sealing component 140 form a seal for the vent 124, but it can also form a wall for the fill chamber 122 so that the sample can be contained therein. Properties incorporated onto the adhesive side of the first sealing component 140 can be associated with the fill chamber 122. For example, if the first sealing component 140 includes properties making it hydrophilic and/or water soluble, the fill chamber can remain wetted when a sample is disposed therein. Further, the sealing components 140, 142 can be selectively associated and disassociated with the immunosensor 110 to provide venting and/or sealing for the immunosensor 110 and the components disposed therein as desired.

Adhesives can generally be used in the construction of the immunosensor. Non-limiting examples of ways in which adhesives can be incorporated into immunosensors and other sample analyzing devices of the present disclosure can be found in U.S. patent application Ser. No. 12/570,268 of Chatelier et al., entitled "Adhesive Compositions for Use in an Immunosensor" and filed on Sep. 30, 2009, the contents of which was already incorporated by reference in its entirety.

While the present disclosure discusses a variety of different embodiments related to immunosensors, other embodiments of immunosensors can also be used with the methods of the present disclosure. Non-limiting examples of such embodiments include those described in U.S. Patent Application Publication No. 2003/0180814 of Hodges et al., entitled "Direct Immunosensor Assay" and filed on Mar. 21, 2002, U.S. Patent Application Publication No. 2004/0203137 of Hodges et al., entitled "Immunosensor" and filed on Apr. 22, 2004, U.S. Patent Application Publication No. 2006/0134713 of Rylatt et al., entitled "Biosensor Apparatus and Methods of Use" and filed on Nov. 21, 2005, and U.S. patent application Ser. No. 12/563,091, which claims priority to each of U.S. Patent Application Publication Nos. 2003/0180814 and 2004/0203137, each of which is hereby incorporated by reference in its entirety.

In one embodiment, the immunosensor 110 can be configured to be placed into a meter that is configured, e.g., via a suitable circuit, to apply a potential to the electrodes 112, 114 and measure a current that results from the application of the potential. In one embodiment, the immunosensor includes one or more tabs 117 for engaging a meter. Other features can also be used to engage the immunosensor 110 with a meter. The meter can include a number of different features. For example, the meter can include a magnet that is configured to maintain certain components of the immunosensor 110 in one chamber while other components flow to the other. In one exemplary embodiment, the magnet of the meter is located such that, upon placing the immunosensor 110 in the meter, the magnet is disposed below the reaction chamber 118. This can allow the magnet to assist in holding back any magnetic beads 134, and more particularly any antibody-enzyme conjugate that is bound to the beads 134, from flowing into the detection chamber 120.

An alternate feature of the meter includes a heating element. A heating element can help speed up the reaction rate and help the sample flow through the immunosensor 110 in a desired manner by reducing the viscosity. A heating element can also allow one or more chambers and/or a sample disposed therein to be heated to a predetermined temperature. Heating to a predetermined temperature can help provide accuracy, for example, by diminishing or removing the effects of temperature change as reactions occur.

Further, a piercing instrument can also be associated with the meter. The piercing instrument can be configured to pierce at least one of the first and second sealing components at a desired time so that air can flow out of the vent hole and liquid can flow from the reaction chamber into the detection chamber.

The immunosensor 110 and the test strip 62 can also be configured to be associated with a control unit. The control unit can be configured to perform a variety of functions. In one exemplary embodiment, the control unit is capable of measuring a fill time of a sample when it is introduced to the device. In another embodiment, the control unit can be configured to determine a haematocrit value of a blood sample. In yet another embodiment, the control unit can is configured to calculate a concentration of an analyte in the sample in view of the fill time. In fact, the control unit can include a number of different features, depending, at least in part, on the functionality desired and the method by which the system is designed to measure the fill time.

The control unit can also measure other aspects of the system. By way of non-limiting example, the control unit can be configured to measure a temperature of one or more chambers of the immunosensor or test strip. It can also be configured to measure a temperature of the sample, a color of the sample, a capacitance of the immunosensor or test strip or a variety of other characteristics and/or properties of the sample and/or the system. By way of further non-limiting example, the control unit can be configured to communicate the results of the fill time determination, the results of the capacitance measurement, the results of the analyte concentration determination, and/or the haematocrit measurement to outside equipment. This can be accomplished in any number of ways. In one embodiment, the control unit can be hardwired to a microprocessor and/or a display device. In another embodiment, the control unit can be configured to wirelessly transmit data from the control unit to a microprocessor and/or a display device.

Other components of the system can also be configured to make such measurements. For example, the immunosensor or the meter can be configured to measure a temperature of one or more chambers of the immunosensor or test strip, measure or infer the temperature of a sample, or measure, determine, or infer a variety of other characteristics and/or properties of the sample and/or the system. Still further, one skilled in the art will recognize that these features of a control unit can be interchanged and selectively combined in a single control unit. For example, a control unit can both determine a fill time, a capacitance, and measure a temperature of a chamber. In other embodiments, multiple control units can be used together to perform various functions, based at least in part on the configurations of the various control units and the desired functions to be performed.

Analyte Concentration Test

Figure 7A:
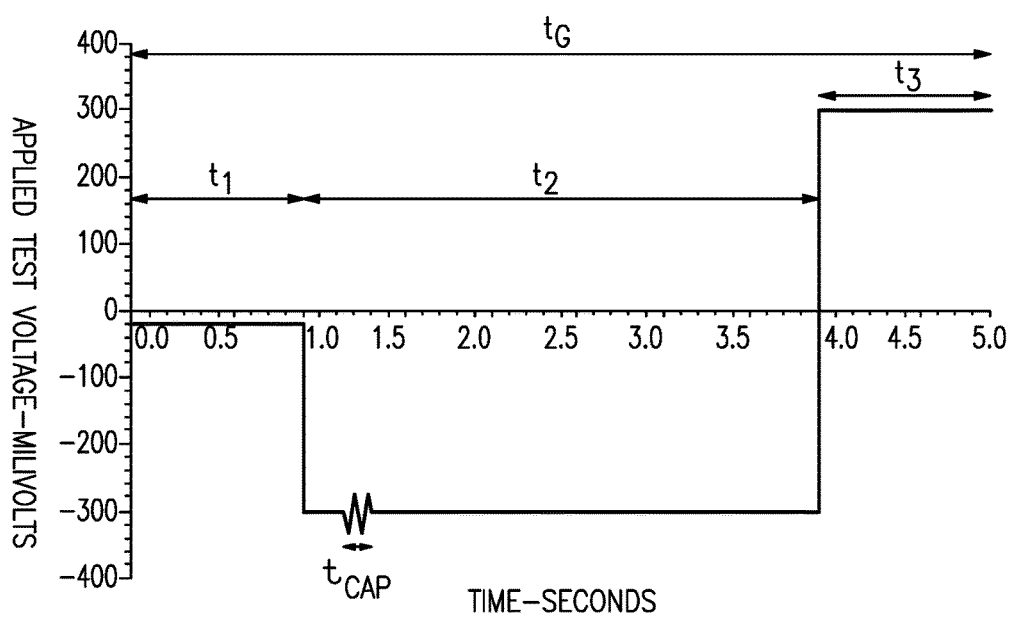
FIG. 7A illustrates a test voltage waveform in which the test meter applies a plurality of test voltages for prescribed time intervals.

In operation, for one embodiment, once the test meter 100 has determined that a fluid has been introduced (e.g., dosed) onto the test strip 62, a test meter 100 can perform an analyte test by applying a plurality of test potentials to the test strip 62 for prescribed intervals as shown in FIG. 7A. An analyte test time interval $t_G$, represents an amount, of time to perform the analyte test (but not necessarily all the calculations associated with the analyte test) where the analyte test time interval $t_G$ can include a first test potential $E_1$ for a first test potential time interval $t_1$, a second test potential $E_2$ for a second test potential time interval $t_2$, and a third test potential $E_3$ for a third test potential time interval $t_3$. Further, as illustrated in FIG. 7A, the second test potential time interval $t_2$ can include a constant (DC) test voltage component and a superimposed alternating (AC), or oscillating, test voltage component. The superimposed alternating test voltage component can be applied for a time interval indicated by $t_{cap}$. The glucose test time interval $t_G$ can range, for example, from about 1 second to about 5 seconds.

As discussed above, either the first electrode 166 or the second electrode 164 can function as working electrode which oxidizes or reduces a limiting amount of mediator depending on the polarity of the applied test potential of the test meter. It should be noted that unless otherwise stated all potentials applied by test meter 100 will hereinafter be stated with respect to second electrode 164. However, applicants note that the test potentials applied by test meter 100 can also be stated with respect to the first electrode 166, in which case the polarity of the test potentials and measured currents discussed below would be reversed.

The plurality of test current values measured during the first, second, and third test potential time intervals may be performed at a frequency ranging from about 1 measurement per approximately 1 nanosecond to about one measurement per approximately 100 milliseconds. Applicants note that names "first," "second," and "third" are chosen for convenience and do not necessarily reflect the order in which the test potentials are applied. For instance, an embodiment can have a potential waveform where the third test voltage can be applied before the application of the first and second test voltage. While an embodiment using three test voltages in a serial manner is described, applicants note that the analyte test can include different numbers of open-circuit and test voltages. Applicants note that the analyte test time interval can include any number open-circuit potential time intervals. For example, the analyte test time interval could include only two test potential time intervals and/or open circuit potential time intervals before and/or after one or more test potential time intervals. In another exemplary embodiment, the analyte test could include an open-circuit for a first time interval, a second test voltage for a second time interval, and a third test voltage for a third time interval.

As shown in FIG. 7A, the test meter 100 may apply a first test potential $E_1$ (e.g., about −20 mV as illustrated in FIG. 7A) for a first test potential time interval $t_1$ (e.g., in the range of about 0 to about 1 second). The first test potential time interval $t_1$ can range from about 0.1 seconds to about 3 seconds and preferably range from about 0.2 seconds to about 2 seconds, and most preferably range from about 0.3 seconds to about 1 seconds from an initiation point of zero (0) seconds in FIG. 7A. The first test potential time interval $t_1$ may be sufficiently long so that the sample reaction chamber 61 can fully fill with sample and also so that the reagent layer 72 can at least partially dissolve or solvate. In other embodiments, the first test potential time interval $t_1$ can include any other desired time ranges.

In one embodiment, the test meter 100 can apply a first test potential $E_1$ between the electrodes for a duration between when the meter can detect that the strip is filling with sample and before a second test potential $E_2$ is applied. In one aspect, the test potential $E_1$ is small. For example, the potential can be in the range of about −1 to about −100 mV, preferably in the range of about −5 mV to about −50 mV and most preferably in the range of about −10 mV to about −30 mV. The smaller potential perturbs the reduced mediator concentration gradient to a lesser extent compared to applying a larger potential difference, but is still sufficient to obtain a measure of the oxidizable substances in the sample. The test potential $E_1$ can be applied for a portion of the time between detection of fill and when the second test potential $E_2$ is applied or can be applied for the whole of that time period. If the test potential $E_1$ is to be used for a portion of the time then an open-circuit could be applied for the remaining portion of the time. The combination of any number of open-circuit and small voltage potential applications, their order and times applied is not critical in this embodiment, can be applied as long as the total period for which the small potential $E_1$ is applied is sufficient to obtain a current measurement indicative of the presence and/or quantity of oxidizable substances present in the sample. In a preferred embodiment, the small potential $E_1$ is applied for substantially the entire period between when a fill is detected and when the second test potential $E_2$ is applied.

During the first time interval $t_1$, the test meter 100 measures the resulting first current transient, which can be referred to as $i_a(t)$. A current transient represents a plurality of current values measured by a test meter during a particular test potential time interval. The first current transient can be an integral of current values over the first test potential time interval, or an average or single current value measured during the first test potential time interval multiplied by the time interval of the first test potential time interval. In some embodiments, the first current transient can include current values measured over various time intervals during the first test potential time interval. In one embodiment, the first current transient $i_a(t)$ can be measured for a time in the range of about 0.05 seconds to about 1.0 second and preferably in the range of about 0.1 seconds to about 0.5 seconds, and most preferably in the range of about 0.1 seconds to about 0.2 seconds. In other embodiments, the first current transient $i_a(t)$ can be measured for other desired time ranges. As discussed below, a portion or all of the first current transient can be used in the methods described herein to determine whether a control solution or a blood sample was applied to the test strip 62. The magnitude of the first transient current is affected by the presence of easily oxidizable substances in the sample. Blood usually contains endogenous and exogenous compounds that are easily oxidized at second electrode 164. Conversely, the control solution can be formulated such that it does not contain oxidizable compounds. However, blood sample composition can vary and the magnitude of the first current transient for high viscosity blood samples will typically be smaller than low viscosity samples (in some cases even less than the control solution samples) because the sample reaction chamber 61 may be not be completely filled after about 0.2 seconds. An incomplete fill will cause the effective area of the first electrode 166 and the second electrode 164 to decrease which in turn can cause the first current transient to decrease. Thus, the presence of oxidizable substances in a sample, by itself, is not always a sufficient discriminatory factor because of variations in blood samples.

Once the first time interval $t_1$ time has elapsed, the test meter 100 can apply a second test potential $E_2$ between the first electrode 166 and the second electrode 164 (e.g., about −300 mV as illustrated in FIG. 7A) for a second test potential time interval $t_2$ (e.g., about 3 seconds as illustrated in FIG. 7A). The second test potential $E_2$ may be a value sufficiently negative of the mediator redox potential so that a limiting oxidation current occurs at the second electrode 164. For example, when using ferricyanide and/or ferrocyanide as the mediator, the second test potential $E_2$ can range from about −600 mV to about zero mV, preferably range from about −600 mV to about −100 mV, and more preferably be about −300 mV. Likewise, the time interval indicated as $t_{cap}$ in FIG. 6 may also last over a range of times, but in one exemplary embodiment it has a duration of about 20 milliseconds. In one exemplary embodiment, the superimposed alternating test voltage component is applied after about 0.3 seconds to about 0.32 seconds after the application of the second test potential $E_2$, and induces two cycles of a sine wave having a frequency of about 109 Hz with an amplitude of about +/−50 mV. During the second test potential time interval $t_2$, the test meter 100 can measure a second current transient $i_b(t)$.

The second test potential time interval $t_2$ may be sufficiently long to monitor the rate of generation of reduced mediator (e.g., ferrocyanide) in the sample reaction chamber 61 based on the magnitude of a limiting oxidation current. The reduced mediator may be generated by a series of chemical reactions in the reagent layer 72. During the second test potential time interval $t_2$, a limiting amount of reduced mediator is oxidized at the second electrode 164 and a non-limiting amount of oxidized mediator is reduced at the first electrode 166 to form a concentration gradient between the first electrode 166 and the second electrode 164. As will be described, the second test potential time interval $t_2$ should be sufficiently long so that a sufficient amount of ferricyanide can be generated at the second electrode 164. A sufficient amount of ferricyanide may be required at the second electrode 164 so that a limiting current can be measured for oxidizing ferrocyanide at the first electrode 166 during the third test potential $E_3$. The second test potential time interval $t_2$ can range from about 0 seconds to about 60 seconds and preferably range from about 1 second to about 10 seconds, and most preferably range from about 2 seconds to about 5 seconds.

Figure 7B:
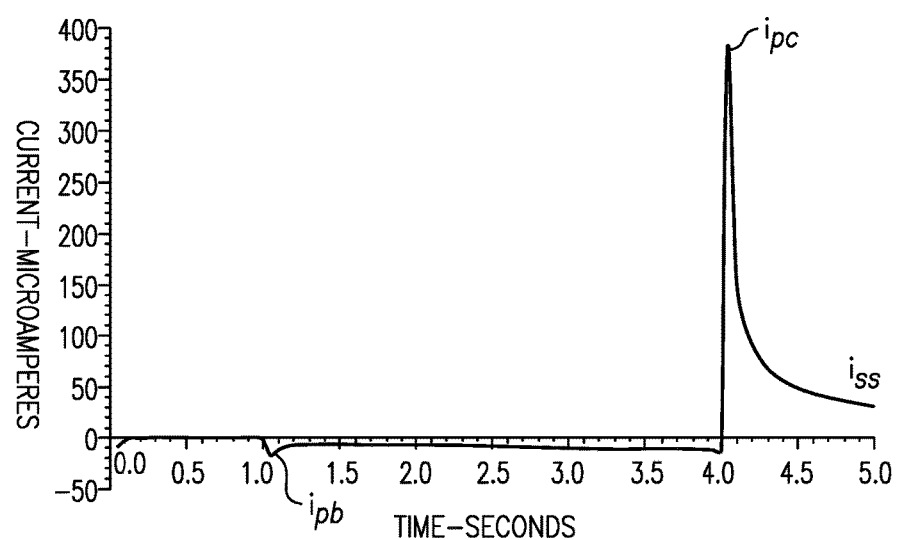
FIG. 7B illustrates a test current transient generated with the test voltage waveform of FIG. 6.

FIG. 7B shows a relatively small peak $i_{pb}$ at the beginning of the second test potential time interval $t_2$ followed by a gradual increase of an absolute value of an oxidation current during the second test potential time interval (e.g., in the range of about 1 second to about 4 seconds). The small peak occurs due to an initial depletion of reduced mediator at about 1 second. The gradual increase in oxidation current is ascribed to the generation of ferrocyanide by reagent layer 72 followed by its diffusion to the second electrode 164.

After the second potential time interval $t_2$ has elapsed, the test meter 100 can apply a third test potential $E_3$ between the first electrode 166 and the second electrode 164 (e.g., about +300 mV as illustrated in FIG. 7A) for a third test potential time interval $t_3$ (e.g., in the range of about 4 to about 5 seconds as illustrated in FIG. 6). During the third test potential time interval $t_3$, the test meter 100 can measure a third current transient, which may be referred to as $i_c(t)$. The third test potential $E_3$ may be a value sufficiently positive of the mediator redox potential so that a limiting oxidation current is measured at the first electrode 166. For example, when using ferricyanide and/or ferrocyanide as the mediator, the magnitude of the third test potential $E_3$ can range from about zero mV to about 600 mV, preferably range from about 100 mV to about 600 mV, and more preferably be about 300 mV.

The second test potential time interval $t_2$ and the third test potential time interval $t_3$ can each range from about 0.1 seconds to about 4 seconds. For the embodiment shown in FIG. 7A, the second test potential time interval $t_2$ was about 3 seconds and the third test potential time interval $t_3$ was about 1 second. As mentioned above, an open circuit potential time period can be allowed to elapse between the second test potential $E_2$ and the third test potential $E_3$. Alternatively, the third test potential $E_3$ can be applied following the application of the second test potential $E_2$. Note that a portion of the first, second, or third current transient may be generally referred to as a cell current or a current value.

The third test potential time interval $t_3$ may be sufficiently long to monitor the diffusion of a reduced mediator (e.g., ferrocyanide) near the first electrode 166 based on the magnitude of the oxidation current. During the third test potential time interval $t_3$, a limiting amount of reduced mediator is oxidized at the first electrode 166 and a non-limiting amount of oxidized mediator is reduced at the second electrode 164. The third test potential time interval $t_3$ can range from about 0.1 seconds to about 5 seconds and preferably range from about 0.3 seconds to about 3 seconds, and most preferably range from about 0.5 seconds to about 2 seconds.

FIG. 7B shows a relatively large peak at the beginning of the third test potential time interval $t_3$ followed by a decrease to a steady-state current. In one embodiment, the first test potential $E_1$ and the second test potential $E_2$ both have a first polarity, and the third test potential $E_3$ has a second polarity, which is opposite to the first polarity. However, applicants note that the polarity of the first, second, and third test potentials can be chosen depending on the manner in which analyte concentration is determined and/or depending on the manner in which the test samples and control solutions are distinguished.

Capacitance Measurement

In some embodiments, a capacitance can be measured. The capacitance measurement can measure essentially an ionic double-layer capacitance resulting from the formation of ionic layers at the electrode-liquid interface. A magnitude of the capacitance can be used to determine whether a sample is control solution or a blood sample. For example, when a control solution is within the reaction chamber, the magnitude of the measured capacitance can be greater than the magnitude of the measured capacitance when a blood sample is in the reaction chamber. As will be discussed in more detail below, a measured capacitance can be used in various methods to correct for the effects of changes in a physical property of the electrochemical cell on measurements made using the electrochemical cell. For example, changes in the measured capacitance can be related to at least one of an age of the electrochemical cell and a storage condition of the electrochemical cell.

By way of non-limiting example, methods and mechanisms for performing capacitance measurements on test strips can be found in U.S. Pat. Nos. 7,195,704 and 7,199,594, each of which is hereby incorporated by reference in its entirety. In one exemplary method for measuring capacitance, a test voltage having a constant component and an oscillating component is applied to the test strip. In such an instance, the resulting test current can be mathematically processed, as described in further detail below, to determine a capacitance value.

Generally, when a limiting test current occurs at a working electrode having a well-defined area (i.e., an area not changing during the capacitance measurement), the most accurate and precise capacitance measurements in an electrochemical test strip can be performed. A well-defined electrode area that does not change with time can occur when there is a tight seal between the electrode and the spacer. The test current is relatively constant when the current is not changing rapidly due either to analyte oxidation or electrochemical decay. Alternatively, any period of time when an increase in signal, which would be seen due to analyte oxidation, is effectively balanced by a decrease in signal, which accompanies electrochemical decay, can also be an appropriate time interval for measuring capacitance.

An area of first electrode 166 can potentially change with time after dosing with the sample if the sample seeps in between the spacer 60 and the first electrode 166. In an embodiment of a test strip, reagent layer 72 can be have an area larger than the cutout area 68 that causes a portion of the reagent layer 72 to be in between the spacer 60 and the first electrode layer 66. Under certain circumstances, interposing a portion of the reagent layer 72 in between the spacer 60 and the first electrode layer 66 can allow the wetted electrode area to increase during a test. As a result, a leakage can occur during a test that causes the area of the first electrode to increase with time, which in turn can distort a capacitance measurement.

In contrast, an area of second electrode 164 can be more stable with time compared to the first electrode 166 because there is no reagent layer in between the second electrode 164 and the spacer 60. Thus, the sample is less likely to seep in between the spacer 60 and the second electrode 164. A capacitance measurement that uses a limiting test current at the second electrode 164 can thus be more precise because the area does not change during the test.

As discussed above and as shown in FIG. 7A, once liquid is detected in the test strip, first test potential $E_1$ (e.g., about −20 mV, as illustrated in FIG. 7A) can be applied between the electrodes for about 1 second to monitor the fill behavior of the liquid and to distinguish between control solution and blood. In Equation 1, the test currents are used from about 0.05 to about 1 second. This first test potential $E_1$ can be relatively low such that the distribution of ferrocyanide in the cell is disturbed as little as possible by the electrochemical reactions occurring at the first and second electrodes.

A second test potential $E_2$ (e.g., about −300 mV, as illustrated in FIG. 7A) having a larger absolute magnitude can be applied after the first test potential $E_1$ such that a limiting current can be measured at the second electrode 164. The second test potential $E_2$ can include an AC voltage component and a DC voltage component. The AC voltage component can be applied at a predetermined amount of time after the application of the second test potential $E_2$, and further, can be a sine wave having a frequency of about 109 Hertz and an amplitude of about +/−50 millivolts. In a preferred embodiment, the predetermined amount of time can range from about 0.3 seconds to about 0.4 seconds after the application of the second test potential $E_2$. Alternatively, the predetermined amount of time can be a time where a test current transient as a function of time has a slope of about zero. In another embodiment, the predetermined amount of time can be a time required for a peak current value (e.g., $i_{pb}$) to decay by about 50%. As for the DC voltage component, it can be applied at a beginning of the first test potential. The DC voltage component can have a magnitude sufficient to cause a limiting test current at the second electrode such as, for example, about −300 mV with respect to the second electrode.

Figure 4A:
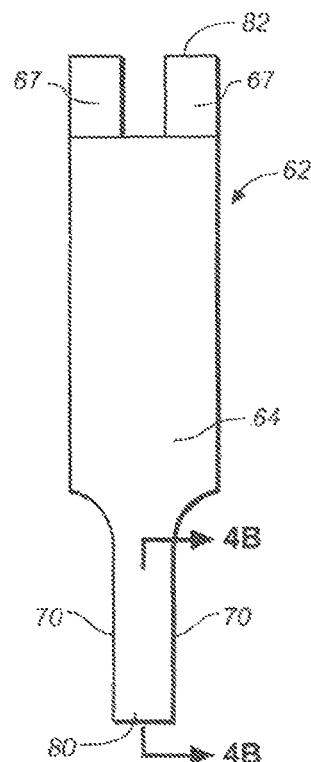
FIG. 4A illustrates a top plan view of the test strip of FIG. 1A.
Figure 4B:
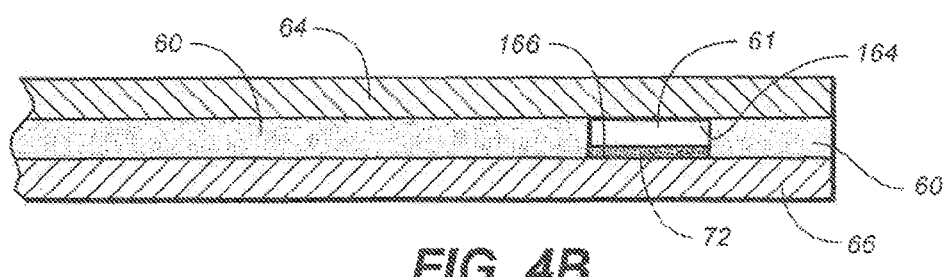
FIG. 4B illustrates a partial side view of the distal portion of the test strip consistent with arrows 4B-4B of FIG. 4A.

Consistent with FIG. 4B, the reagent layer 72 is not coated onto the second electrode 164, which causes the magnitude of the absolute peak current $i_{pb}$ to be relatively low compared to the magnitude of the absolute peak current $i_{pc}$. The reagent layer 72 can be configured to generate a reduced mediator in a presence of an analyte, and the amount of the reduced mediator proximate to first electrode can contribute to the relatively high absolute peak current $i_{pc}$. In one embodiment at least the enzyme portion of the reagent layer 72 can be configured to not substantially diffuse from the first electrode to the second electrode when a sample is introduced into the test strip.

The test currents after $i_{pb}$ tends to settle to a flat region at approximately 1.3 seconds, and then the current increases again as the reduced mediator generated at the first electrode 166, which can be coated with the reagent layer 72, diffuses to the second electrode 164, which is not coated with the reagent layer 72. In one embodiment, a capacitance measurement can be performed at a relatively flat region of the test current values, which can be performed at about 1.3 seconds to about 1.4 seconds. Generally, if the capacitance is measured before 1 second, then the capacitance measurement can interfere with the relatively low first test potential $E_1$ that can be used to measure the first current transient $i_a(t)$. For example, an oscillating voltage component on the order of ±50 mV superimposed onto a −20 mV constant voltage component can cause significant perturbation of the measured test current. Not only does the oscillating voltage component interfere with the first test potential $E_1$, but it can also significantly perturb the test currents measured at about 1.1 seconds, which in turn can interfere with correction for antioxidants. Following a great deal of testing and experimentation, it was finally determined that, surprisingly, measuring the capacitance at about 1.3 seconds to about 1.4 seconds resulted in accurate and precise measurements that did not interfere with the control solution/blood discrimination test or the blood analyte (e.g., glucose) algorithm.

After the second test potential $E_2$, third test potential $E_3$ (e.g., about +300 mV, as illustrated in FIG. 7A) can be applied causing the test current to be measured at the first electrode 166, which can be coated with the reagent layer 72. The presence of a reagent layer on the first electrode can allow penetration of liquid between the spacer layer and the electrode layer, which can cause the electrode area to increase.

As illustrated in FIG. 7A, in an exemplary embodiment a 109 Hz AC test voltage (±50 mV peak-to-peak) can be applied for 2 cycles during the time interval $t_{cap}$. The first cycle can be used as a conditioning pulse and the second cycle can be used to determine the capacitance. The capacitance estimate can be obtained by summing the test current over a portion of the alternating current (AC) wave, subtracting the direct current (DC) offset, and normalizing the result using the AC test voltage amplitude and the AC frequency. This calculation provides a measurement of the capacitance of the strip, which is dominated by the strip sample chamber when it is filled with a sample.

In one embodiment for blood glucose assay, the capacitance can be measured by summing the test current over one quarter of the AC wave on either side of the point in time where the input AC voltage crosses the DC offset, i.e. when the AC component of the input voltage is zero (the zero crossing point). A derivation of how this translates to a measurement of the capacitance is described in further detail below. Equation 1 can show the test current magnitude as a function of time during the time interval $t_{cap}$:

$$i(t) = i_o + st + I\sin(\omega t + \phi) \qquad \text{Eq. 1}$$

where the terms $i_o + st$ represent the test current caused by the constant test voltage component. Generally, the DC current component is considered as changing linearly with time (due to the on-going glucose reaction generating ferrocyanide) and is thus represented by a constant $i_o$, which is the DC current at time zero (the zero crossing point), and s, the slope of the DC current change with time. The AC current component is represented by $I\sin(\omega t + \phi)$, where I is the amplitude of the current wave, $\omega$ is its frequency, and $\phi$ is its phase shift relative to the input voltage wave. The term $\omega$ can also be expressed as $2\pi f$, where f is the frequency of the AC wave in Hertz. The term I can also be expressed as shown in Equation 2:

$$I = \frac{V}{|Z|} \qquad \text{Eq. 2}$$

where V is the amplitude of the applied voltage signal and $|Z|$ is the magnitude of the complex impedance. The term $|Z|$ can also be expressed as shown in Equation 22:

$$|Z| = \frac{R}{\sqrt{1 + \tan^2\phi}} = \frac{R}{\sqrt{1 + \omega^2 R^2 C^2}} \qquad \text{Eq. 3}$$

where R is the real part of the impedance and C is the capacitance.

Equation 1 can be integrated from one quarter wavelength before the zero crossing point to one quarter wavelength after the zero crossing point to yield Equation 4:

$$\int_{-\frac{1}{4f}}^{\frac{1}{4f}} i(t) = i_o[t]_{-\frac{1}{4f}}^{\frac{1}{4f}} + \frac{s}{2}[t^2]_{-\frac{1}{4f}}^{\frac{1}{4f}} + I\int_{-\frac{1}{4f}}^{\frac{1}{4f}} \sin(\omega t + \phi), \qquad \text{Eq. 4}$$

which can be simplified to Equation 5:

$$\int_{-\frac{1}{4f}}^{\frac{1}{4f}} i(t) = \frac{i_o}{2f} + \frac{I\sin\phi}{\pi f}. \qquad \text{Eq. 5}$$

By substituting Eq. 2 into Eq. 1, then into Eq. 4, and then rearranging, Equation 6 results:

$$C = \frac{1}{2V}\left(\int_{-\frac{1}{4f}}^{\frac{1}{4f}} i(t) - \frac{i_o}{2f}\right). \qquad \text{Eq. 6}$$

The integral term in Equation 6 can be approximated using a sum of currents shown in an Equation 7:

$$\int_{-\frac{1}{4f}}^{\frac{1}{4f}} i(t) \approx \frac{\frac{1}{n}\sum_{k=1}^{n} i_k}{2f} \qquad \text{Eq. 7}$$

where the test currents $i_k$ are summed from one quarter wavelength before the zero crossing point to one quarter wavelength past the zero crossing point. Substituting Equation 7 into Equation 6 yields Equation 8:

$$C = \frac{\frac{1}{n}\sum_{k=1}^{n} i_k - i_o}{4Vf}, \qquad \text{Eq. 8}$$

in which the DC offset current $i_o$ can be obtained by averaging the test current over one full sine cycle around the zero crossing point.

In another embodiment, the capacitance measurements can be obtained by summing the currents not around the voltage zero crossing point, but rather around the maximum AC component of the current. Thus, in Equation 7, rather than summing a quarter wavelength on either side of the voltage zero crossing point, the test current can be summed a quarter wavelength around the current maximum. This is tantamount to assuming that the circuit element responding to the AC excitation is a pure capacitor, so $\phi$ is approximately $\pi/2$. Thus, Equation 5 can be reduced to Equation 9:

$$\int_{-\frac{1}{4f}}^{\frac{1}{4f}} i(t) = \frac{i_o}{2f} + \frac{I}{\pi f}. \qquad \text{Eq. 9}$$

This is believed to be a reasonable assumption in this case as the uncoated electrode is polarized such that the DC, or real, component of the current flowing is independent of the voltage applied over the range of voltages used in the AC excitation. Accordingly, the real part of the impedance responding to the AC excitation is infinite, implying a pure capacitive element. Equation 9 can then be used with Equation 6 to yield a simplified capacitance equation that does not require an integral approximation. The net result is that capacitance measurements when summing the currents not around the voltage crossing point, but rather around the maximum AC component of the current, were more precise.

CS/Blood Discrimination Test

In some embodiments, a control solution (CS)/blood discrimination test can be performed. If the CS/blood discrimination test determines that the sample is blood, then a series of steps can be performed that can include: the application of a blood glucose algorithm, hematocrit correction, blood temperature correction, and error checks; and if the CS/blood discrimination test determines that the sample is CS (i.e., not blood), then a series of steps can be performed that can include: the application of a CS glucose algorithm, CS temperature correction, and error checks. If there are no errors, then the test meter outputs a glucose concentration, but if there are errors, then the test can output an error message.

In one embodiment, characteristics of a control solution (CS) are used to distinguish control solutions from blood. For example, the presence and/or concentration of redox species in the sample, reaction kinetics, and/or capacitance can be used to distinguish control solutions from blood. The method disclosed herein can include the step of calculating a first reference value that is representative of the redox concentration in the sample and a second reference value that is representative of the rate of reaction of the sample with the reagent. In one embodiment, the first reference value is an interferent oxidation current and the second reference value is a reaction completion index.

In some embodiments, a third reference value can be calculated by multiplying the first reference value by a capacitance index. The capacitance index can be any calculated value that is a capacitance or is related to, e.g., proportional to, a capacitance value. The capacitance index, for example, can be a measured capacitance, a known or predetermined capacitance, or any combination thereof. The capacitance index can also be related to any of the aforementioned capacitances and an empirically derived constant. In an exemplary embodiment, the capacitance index can be a ratio of a known capacitance to a measured capacitance or a ratio of a measured capacitance to a known capacitance. The known capacitance can be an average capacitance measured when blood samples are loaded into test strips of the same type as the test strip being used for the current test. The measured capacitance can be measured using the algorithm discussed above, for example.

In one embodiment, a CS/blood discrimination test can include a first reference value and a second reference value. The first value can be calculated based on the current values within the first time interval $t_1$ and the second reference value can be based on current values during both the second time interval $t_2$ and the third time interval $t_3$. In one embodiment the first reference value can be obtained by performing a summation of the current values obtained during the first time current transient when using the test voltage waveform of FIG. 7A. By way of non-limiting example, a first reference value $i_{sum}$ can be represented by Equation 10A:

$$i_{sum} = \sum_{t=0.05}^{1} i(t) \qquad \text{Eq. 10A}$$

where the term $i_{sum}$ is the summation of current values and t is a time. In some embodiments, the first reference value can be multiplied by a capacitance index where the capacitance index can be a ratio of a known capacitance to a measured capacitance. In such embodiments, a third reference value $i_{capsum}$ can be represented by Equation 10B:

$$i_{capsum} = \frac{C_{av}}{C_m} \sum_{t=0.05}^{1} i(t) \qquad \text{Eq. 10B}$$

where $C_{av}$ is a known average capacitance, $C_m$ is a measured capacitance, and t is a time. In an exemplary embodiment of Equation 10B, the ratio of $C_{av}$ to $C_m$ can be referred to as the capacitance index. In one exemplary embodiment, the known average capacitance $C_{av}$ for an exemplary test strip according to an embodiment of the present invention is about 582 nanofarads.

The second reference value, sometimes referred to as the residual reaction index, can be obtained by a ratio Y of current values during the second time interval and the third time interval, as shown in Eq. 11:

$$Y = \text{abs}\left(\frac{i(3.8)}{i(4.15)}\right) \quad \text{Eq. 11}$$

where abs represents an absolute value function and 3.8 and 4.15 represent the time in seconds of the second and third time intervals, respectively, for this particular example.

A discrimination criterion can be used to determine if the sample is either control solution or blood based on the first reference value of Eq. 10A or the third reference value of Eq. 10B, and the second reference of Eq. 11. For example, the first reference value of Eq. 10A or the third reference value of Eq. 10B can be compared to a pre-determined threshold and the second reference value of Eq. 11 can be compared to a pre-determined threshold function. The pre-determined threshold may be, for example, about 12 microamperes. The pre-determined threshold function can be based on a function using the first reference value of Eq. 10A or Eq. 10B. More specifically, as illustrated by Eq. 12, where the calculated value of either of $i_{sum}$ in Eq. 10A or $i_{capsum}$ in Eq. 10B is represented by X, the pre-determined threshold function $F_{pdt}$ can be:

$$F_{PDT} = Z\frac{X - 12}{X} \quad \text{Eq. 12}$$

where Z can be a constant such as, for example, about 0.2. Thus, the CS/Blood discrimination test can identify a sample as blood if $i_{sum}$ in Eq. 10A or $i_{capsum}$ in Eq. 10B is greater than or equal to the predetermined threshold, e.g., about 12 microamperes, and if the ratio Y of current values during the second time interval and the third time interval, as shown in Eq. 11, is less than the value of the pre-determined threshold function $F_{pdt}$, else the sample is a control solution. In one embodiment, the CS/blood discrimination test can also be represented, for example, by Eq. 13:

$$\text{If } i_{capsum} \geq 12 \text{ and } Y < Z\frac{i_{capsum} - 12}{i_{capsum}}, \quad \text{Eq. 13}$$

then sample is blood, else control solution.

Non-limiting examples of the embodiments discussed above include those described in U.S. patent application Ser. No. 12/895,067 of Chatalier et al., entitled "Systems and Methods of Discriminating Between a Control Sample and a Test Fluid Using Capacitance" and filed on Sep. 10, 2010, and U.S. patent application Ser. No. 12/895,168 of Chatelier et al., entitled "Systems and Methods for Improved Stability of Electrochemical Sensors" and filed on Sep. 30, 2010, each of which is hereby incorporated by reference in its entirety.

Blood Glucose Algorithm

Figure 8A:
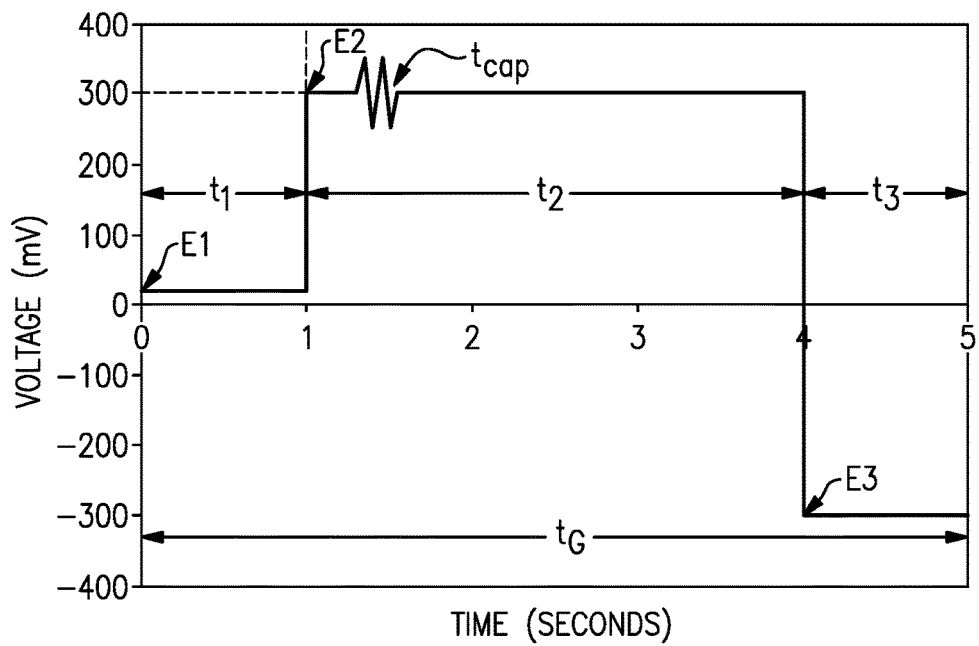
FIG. 8A illustrates a test voltage waveform in which the test meter applies a plurality of test voltages at opposite polarity for prescribed time intervals as compared to FIG. 7A.

If the sample is identified as a blood sample, a blood glucose algorithm can be performed on the test current values. Assuming that a test strip has an opposing face or facing arrangement as shown in FIGS. 1A-4B, and that a potential waveform is applied to the test strip as shown in FIG. 7A or FIG. 8A, a first analyte concentration G1 can be calculated using a glucose algorithm as shown in Equation (Eq.) 14:

$$G1 = \left(\frac{i_r}{i_l}\right)^p \{ai_2 - zgr\} \quad \text{Eq. 14}$$

In Eq. 14, G1 is the glucose concentration, $i_l$ is a first current value, $i_r$ is a second current value, and $i_2$ is an antioxidant-corrected current value, and the terms p, zgr, and a are empirically derived calibration constants. For example, p can be about 0.5246; a can be about 0.03422; and zgr can be about 2.25. In one embodiment of the invention, p may range from about 0.2 to about 4, and preferably from about 0.1 to about 1. The calibration factor a is specific to particular dimensions of the electrochemical cell.

A calibration factor zgr is used to account for the typical background signal which arises from the reagent layer. A presence of an oxidizable species within the reagent layer of the cell before the addition of a sample may contribute to a background signal. For example, if the reagent layer were to contain a small amount of ferrocyanide (e.g., reduced mediator) before the sample was added to the test strip, then there would be an increase in the measured test current which would not be ascribed to the analyte concentration. Because this would cause a constant bias in the overall measured test current for the test strips, this bias can be corrected for using the calibration factor zgr. Similar to the terms p and a, zgr can also be calculated during the calibration process. Exemplary methods for calibrating strip lots are described in U.S. Pat. No. 6,780,645 which is hereby incorporated by reference in its entirety. A derivation of Eq. 13 can be found in a pending U.S. Published Patent Application No. 2007/0074977 (U.S. application Ser. No. 11/240,797), filed on Sep. 30, 2005 and entitled "Method and Apparatus for Rapid Electrochemical Analysis," the entirety of which is hereby incorporated herein by reference. All test current values (e.g., $i_l$, $i_r$, and $i_2$) in Equation 13 use the absolute value of the current.

In one embodiment, current value $i_r$ can be calculated from the third current transient and current value $i_l$ can be calculated from the second current transient. All current values (e.g. $i_r$, $i_l$, and $i_2$) stated in Eq. 14 and in subsequent equations can use the absolute value of the current. Current values $i_r$, $i_l$, can be, in some embodiments, an integral of current values over a time interval of a current transient, a summation of current values over a time interval of a current transient, or an average or single current value of a current transient multiplied by a time interval of the current transient. For the summation of current values, a range of consecutive current measurement can be summed together from only two current values or to all of the current values. Current value $i_2$ can be calculated as discussed below.

For example, where an analyte test time interval is 5 seconds long, $i_l$ may be the sum of currents from 3.9 to 4 seconds of a 5 second long period and $i_r$ may be the sum of currents from 4.25 to 5 seconds of the 5 second analyte test time interval, as shown in Eq. 15A and 15B, below.

$$i_r = \sum_{t=4.25}^{5} i(t) \quad \text{Eq. 15A}$$

$$i_l = \sum_{t=3.9}^{4} i(t) \quad \text{Eq. 15B}$$

A magnitude of current for the first current transient can be described as a function of time by Eq. 16.

$$i_{pb}(t) = i_{ss}\left\{1 + 2\sum_{n=1}^{\infty} \exp\left(\frac{-4\pi^2 n^2 Dt}{L^2}\right)\right\} \quad \text{Eq. 16}$$

The term $i_{ss}$ is the steady-state current following the application of second test potential $E_2$, D is the diffusion coefficient of the mediator, L is the thickness of the spacer. It should be noted that in Eq. 16, t refers to the time elapsed after second test potential $E_2$ was applied. A magnitude of current for the third current transient can be described as a function of time by Eq. 17.

$$i_{pc}(t) = i_{ss}\left\{1 + 4\sum_{n=1}^{\infty} \exp\left(\frac{-4\pi^2 n^2 Dt}{L^2}\right)\right\} \quad \text{Eq. 17}$$

There is a factor of two difference for the exponential term in Eq. 17 as compared to the exponential term in Eq. 16 because the third current transient is generated from the third test potential $E_3$, which was opposite in polarity to the second test potential $E_2$, and was applied immediately after the second test potential $E_2$. It should be noted that in Eq. 17, t refers to the time elapsed after third test potential $E_3$ was applied.

A peak current for second test potential time interval $t_2$ can be denoted as $i_{pb}$ and a peak current for third test potential time interval $t_3$ can be denoted as $i_{pc}$. If both second peak current $i_{pb}$ and third peak current $i_{pc}$ were measured at the same short time after the application of second test potential $E_2$ and third test potential $E_3$ respectively, for example 0.1 seconds, Eq. 16 can be subtracted from Eq. 17 to yield Eq. 18.

$$i_{pc} - 2i_{pb} = -i_{ss} \quad \text{Eq. 18}$$

Because it has been determined that $i_{pb}$ is controlled mainly by interferents, $i_{pc}$ can be used with $i_{pb}$ together to determine a correction factor. For example, as shown below $i_{pc}$ can be used with $i_{pb}$ in a mathematical function to determine a corrected current which is proportional to glucose and less sensitive to interferents.

Eq. 19 was derived to calculate a current $i_2$ which is proportional to analyte concentration and has a relative fraction of current removed that is ascribed to interferents.

$$i_2 = i_r\left(\frac{i_{pc} - 2i_{pb} + i_{ss}}{i_{pc} + i_{ss}}\right) \quad \text{Eq. 19}$$

The term $i_{pb}$ represents a peak current value for the second test potential time interval $t_2$ and the term $i_{pc}$ represents a peak current value for the third test potential time interval $t_3$. The term $i_{ss}$ is an estimate of the steady-state current, which is the current predicted to occur at long times after the application of the third test potential $E_3$ in the absence of on-going chemical reactions. The term $i_{ss}$ was added to both the numerator and denominator of Eq. 19 to allow the numerator to approach zero when no glucose is present. Some examples of methods for calculating $i_{ss}$ can be found in U.S. Pat. Nos. 5,942,102 and 6,413,410, each of which is hereby incorporated by reference in its entirety. The use of peak current values to account for interferents in a physiological sample are described in U.S. Published Patent Application No. 2007/0227912 (U.S. patent application Ser. No. 11/278,341), filed on Mar. 31, 2006 and entitled "Methods and Apparatus for Analyzing a Sample in the Presence of Interferents," the entirety of which is hereby incorporated herein by reference.

In one exemplary embodiment, the antioxidant-corrected current value $i_2$ can be calculated according to Eq. 20.

$$i_2 = i_r\left(\frac{i(4.1) - 2i(1.1) + i_{ss}}{i(4.1) + i_{ss}}\right) \quad \text{Eq. 20}$$

In Eq. 20, i(4.1) comprises an absolute value of the current during a third electric potential $E_3$; i(1.1) comprises an absolute value of the current during a second electric potential $E_2$; and $i_{ss}$ comprises a steady-state current.

In some embodiments, $i_{ss}$ can be calculated according to Eq. 21.

$$i_{ss} = \frac{i(5)}{1 + 4e^{-4\pi^2 D/L^2}} \quad \text{Eq. 21}$$

In Eq. 21, i(5) comprises an absolute value of the current during a third electric potential; πcomp,ises a constant; D comprises a diffusion coefficient of a redox species, and L comprises a distance between the two electrodes.

In some embodiments, a second analyte concentration value can be calculated based on the first analyte concentration value G1. For example, Eq. 22 can be used to calculate a second analyte concentration value G2 that deemphasizes the kinetic correction at low analyte concentrations.

$$G2 = \left(\frac{i_r}{i_l} - AFO\right)^{\{p+kG1\}}\{ai_2 - zgr\} \quad \text{Eq. 22}$$

In Eq. 22, p can be about 0.5246; a can be about 0.03422; $i_2$ can be an antioxidant-corrected current value; AFO can be about 2.88; zgr can be about 2.25; and k can be about 0.0000124. By subtracting an asymmetry factor offset AFO from the asymmetry factor $i_r/i_l$ and raising the new smaller asymmetry factor term to an analyte concentration dependent power term, the effect of kinetic correction at low analyte concentrations can be deemphasized. As a result a higher level of accuracy across a large range of analyte concentrations can be achieved.

Figure 8B:
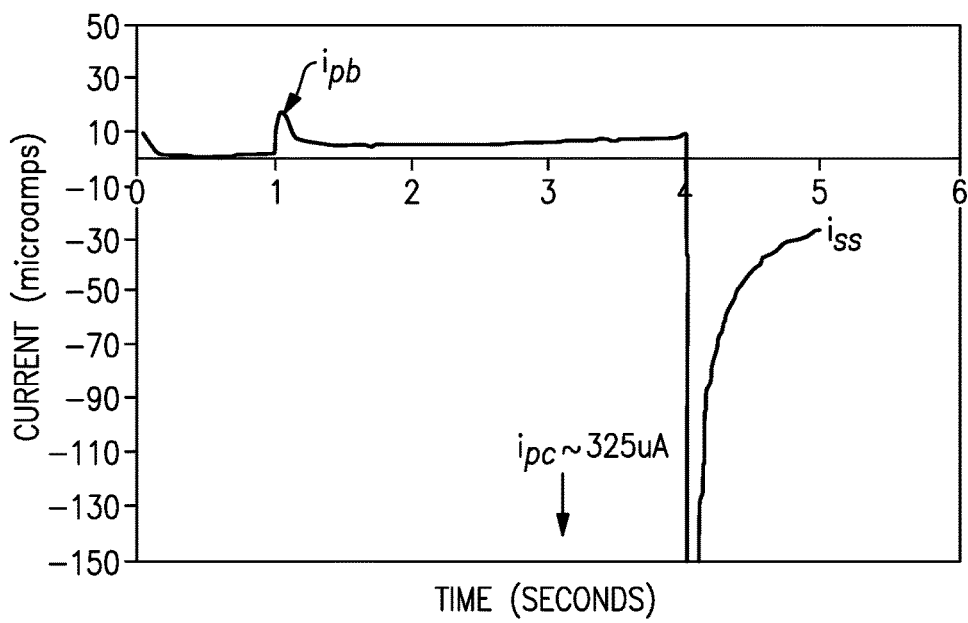
FIG. 8B illustrates a test current transient generated with the test voltages of FIG. 8A.

The example illustrated in FIGS. 7A and 7B shows the polarity of the first and second applied voltages as negative with a third applied voltage as positive when the electrode which is not coated with reagent acts as the reference electrode for the voltage measurement. However, the voltages applied can be of opposite polarity to the sequence illustrated in FIG. 7A if the electrode which is coated with reagent acts as the reference electrode for the voltage measurement. For example, in the preferred embodiment of FIGS. 8A and 8B, the polarity of the first and second applied voltages are positive with the polarity of the third applied voltage as negative. In both cases, the calculation of the glucose is the same because the electrode which is not coated with reagent acts as the anode during the first and second applied voltages, and the electrode which is coated with reagent acts as the anode during the third applied voltage.

In addition, if the test meter determines that the sample is control solution (as opposed to blood), the test meter can store the resulting glucose concentration of the control sample such that a user can review test sample concentration data separately from control solution data. For example, the glucose concentrations for control solutions can be stored in a separate database, can be flagged, and/or discarded (i.e., not stored or stored for a short period of time).

Another advantage of being able to recognize a control solution is that a test meter can be programmed to automatically compare the results (e.g., glucose concentration) of the test of the control solution with the expected glucose concentration of the control solution. For example, the test meter can be pre-programmed with the expected glucose level(s) for the control solution(s). Alternatively, a user could input the expected glucose concentration for the control solution. When the test meter recognizes a control solution, the test meter can compare the measured control solution glucose concentration with the expected glucose concentration to determine if the meter is functioning properly. If the measured glucose concentration is out of the expected range, the test meter can output a warning message to alert the user.

Temperature Correction

In some embodiments of the systems and methods, a blood temperature correction can be applied to the test current values to provide an analyte concentration with an improved accuracy because of a reduced effect from temperature. A method for calculating a temperature corrected analyte concentration can include measuring a temperature value and calculating a temperature correction value $C_T$. The temperature correction value $C_T$ can be based on a temperature value and an analyte concentration, e.g., a glucose concentration. Accordingly, the temperature correction value $C_T$ can then be used to correct the analyte concentration for temperature.

Initially, an analyte concentration uncorrected for temperature can be obtained, such as an analyte concentration G2 from Equation 22, above. A temperature value can also be measured. The temperature can be measured using a thermistor or other temperature reading device that is incorporated into a test meter, or by way of any number of other mechanisms or means. Subsequently, a determination can be performed to determine whether the temperature value T is greater than a first temperature threshold $T_1$. For example, the temperature threshold $T_1$ can be about 15° C. If the temperature value T is greater than 15° C., then a first temperature function can be applied to determine the temperature correction value $C_T$. If the temperature value T is not greater than 15° C., then a second temperature function can be applied to determine the temperature correction value $C_T$.

The first temperature function for calculating the temperature correction value $C_T$ can be in the form of Equation 23:

$$C_T = +K_9(T-T_{RT}) + K_{10}G2(T-T_{RT}) \qquad \text{Eq. 23}$$

where $C_T$ is the correction value, $K_9$ is a ninth constant (e.g., −0.866), T is a temperature value, $T_{RT}$ is a room temperature value (e.g., 22° C.), $K_{10}$ is a tenth constant (e.g., 0.000687), and G2 is the analyte concentration. When T is about equal to $T_{RT}$, $C_T$ is about zero. In some instances, the first temperature function can be configured to have essentially no correction at room temperature such that variation can be reduced under routine ambient conditions. The second temperature function for calculating the second correction value $C_T$ can be in the form of Equation 24:

$$C_T = +K_{11}(T-T_{RT}) + K_{12}G2(T-T_{RT}) + K_{13}(T-T_1) + K_{14}G2(T-T_1) \qquad \text{Eq. 24}$$

where $C_T$ is the correction value, $K_{11}$ is an eleventh constant (e.g., −0.866), T is a temperature value, $T_{RT}$ is a room temperature value, $K_{12}$ is a twelfth constant (e.g., 0.000687), G2 is an analyte concentration, $K_{13}$ is a thirteenth constant (e.g., −0.741), $T_1$ is a first temperature threshold (e.g., about 15° C.), and $K_{14}$ is a fourteenth constant (e.g., 0.00322).

After $C_T$ is calculated using Eq. 23, a couple of truncation functions can be performed to ensure that $C_T$ is constrained to a pre-determined range, thereby mitigating the risk of an outlier. In one embodiment $C_T$ can be limited to have a range of −10 to +10. For example, a determination can be performed to determine whether $C_T$ is greater than 10. If $C_T$ is greater than 10, and the temperature is above a threshold value, e.g., 15° C., then $C_T$ is set to 10. If $C_T$ is not greater than 10, then a determination is performed to determine whether $C_T$ is less than −10. $C_T$ can be set to −10 if $C_T$ is less than −10. If $C_T$ is a value already in between −10 and +10, then there generally is no need for truncation. However, if the temperature is less than a threshold value, e.g., 15° C., then the maximum value of $C_T$ can be set to 10+0.92 (15−T).

Once $C_T$ is determined, a temperature corrected analyte concentration can be calculated. For example, a determination can be performed to determine whether the analyte concentration uncorrected for temperature (e.g., G2) is less than 100 mg/dL. If G2 is less than 100 mg/dL, then an Equation 25 can be used to calculate the temperature corrected analyte concentration G3 by adding the correction value $C_T$ to the glucose concentration G2:

$$G3 = G2 + C_T. \qquad \text{Eq. 24}$$

If G2 is not less than 100 mg/dL, then an Equation 26 can be used to calculate the temperature corrected analyte concentration G2 by dividing $C_T$ by one hundred, adding one; and then multiplying by the analyte concentration G2 (this approach effectively uses $C_T$ as a percentage correction term):

$$G3 = G2[1 + 0.01(C_T)]. \qquad \text{Eq. 26}$$

Once an analyte concentration is determined that has been corrected for the effects of temperature, a further correction can be made based on the fill time of the sample.

Fill Time Correction

In some embodiments, the analyte concentration can be corrected on the basis of the fill time of the sample. One example of such a method is disclosed in a co-pending patent application entitled "Systems, Devices and Methods for Improving Accuracy of Biosensors Using Fill Time," of Ronald C. Chatelier and Alastair M. Hodges, (application Ser. No. 12/649,594) filed on Dec. 30, 2009, and "Systems, Devices and Methods for Improving Accuracy of Biosensors Using Fill Time," of Ronald C. Chatelier and Alastair M. Hodges, (application Ser. No. 12/971,777) filed on Dec. 17, 2010, both of which are hereby incorporated by reference in their entirety. In an alternative embodiment for detecting a concentration of an analyte in a sample, errors can be corrected for based on a determined initial fill velocity rather than a determined fill time. One example of such a method is disclosed in a co-pending patent application entitled "Systems, Devices and Methods for Measuring Whole Blood Haematocrit Based on Initial Fill Velocity," of Ronald C. Chatelier, Dennis Rylatt, Linda Raineri, and Alastair M. Hodges, (Application Ser. No. 12/649,509) filed on Dec. 30, 2009, and which is hereby incorporated by reference in its entirety.

In exemplary embodiments of the corrections for fill time discussed above, the temperature corrected analyte concentration G3 can be corrected in view of the fill time to yield a fill-time corrected analyte concentration value G4 according to Eq. 27A and 27B, below. For example, when G3<100 mg/dL, no correction is necessary and G4 can be the uncorrected value of G3. However, when G3≥100 mg/dL, G3 can be corrected using Eq. 27B in conjunction with Eqs. 28A, 28B, and 28C.

$$G4 = G3 \text{ for } G3 < 100 \text{ mg/dL} \qquad \text{Eq. 27A}$$

$$G4 = G3(1 + C_{FT}/100) \text{ for } G3 \geq 100 \text{ mg/dL} \qquad \text{Eq. 27B}$$

The correction factor $C_{FT}$ in Eq. 27B can be calculated in view of the fill time (FT) based on a series of threshold values of FT. For example, the following equations can be used to calculate $C_{FT}$ using two threshold values of FT, $Th_1$ and $Th_2$.

$$\text{if } Th_1 < FT < Th_2 \text{ then } C_{FT} = FT_f(FT - Th_1) \qquad \text{Eq. 28A}$$

$$\text{if } FT < Th_1 \text{ then } C_{FT} = 0 \qquad \text{Eq. 28B}$$

$$\text{if } FT > Th_2 \text{ then } C_{FT} = 10 \qquad \text{Eq. 28C}$$

In an exemplary embodiment, the threshold value $Th_1$ can be about 0.2 seconds, the threshold value $Th_2$ can be about 0.4 seconds and the fill time factor $FT_f$ can be about 41. For example, when blood fills the sensor in less than about 0.2 seconds, then its fill behavior can be described as close to ideal. Fill times of less than about 0.2 seconds usually occur when the hematocrit is low enough that that the viscosity of the sample has a minimal effect on the fill behavior of the sample. As a consequence of the low hematocrit, most of the glucose is believed to be partitioned into the plasma phase where it can be oxidized rapidly. Under these conditions, there is little need to correct the glucose result for the effect of fill time, and so the correction factor can be set to zero. Alternatively, when the hematocrit in the sample is high, the viscosity of the sample can affect the fill time of the sample. As a result, the sample can take more than about 0.4 seconds to fill the sensor. As a consequence of the high hematocrit, most of the glucose is believe to be partitioned into the red blood cells and so a lower fraction of the glucose is oxidized. Under these conditions, the glucose result can be corrected in view of the fill time. However, it can be important not to over-correct the glucose value, and so, in an exemplary embodiment, the correction factor can be restricted to a maximum of about 10 mg/dL plasma glucose or about 10% of the signal. An empirically-derived linear equation can be used to gradually increase the correction term in the range of about 0 to about 10 as the fill time increases in the range of about 0.2 to about 0.4 seconds.

Age/Storage Correction

In some embodiments of the systems and methods of the present invention, a further correction factor can be applied to the fill-time corrected analyte concentration value G4. This correction factor can be used to provide improved accuracy by correcting for the effect of age and/or storage conditions on sensor performance. For example, a parameter correlating to a physical property of the sensor can be measured and that parameter can be used to calculate a corrected analyte concentration. In some embodiments, the parameter correlating to a physical property of the sensor can be a measured capacitance of the sensor.

The measured capacitance of the sensor, e.g., an electrochemical cell of the type described in more detail above, can be related to the age and/or storage conditions of the sensor. By way of non-limiting example, the capacitance of an electrochemical cell can be affected by the slow flow of the adhesive used in the manufacture of the electrochemical cell from the spacer layer into the sample reaction chamber. As the sensor ages, such as during storage, particularly at elevated temperatures, the adhesive can flow into the reaction chamber and cover the reference and/or counter electrodes of the sensor. For example, the adhesive can cause a reduction in the area of the electrodes, which can affect the accuracy of measurements made by the sensor. The reduction in electrode area can also correlate with a reduction in the capacitance of the sensor. A measured capacitance of the sensor can therefore be used to calculate a correction factor that can be used to improve the accuracy of readings made using the sensor.

In one exemplary embodiment, a method for calculating a corrected analyte concentration can include measuring a physical property of the electrochemical cell, e.g., a capacitance, and calculating a correction factor $C_c$. The correction factor $C_c$ can be based on the measured physical property. Accordingly, the correction factor $C_c$ can be used to calculate a corrected analyte concentration.

Initially, an analyte concentration can be obtained, such as the fill-time corrected analyte concentration value G4, above. A measured capacitance of the sensor can also be obtained, e.g., using the capacitance measurement methods discussed above. Subsequently, a determination can be performed to determine whether the measured capacitance value C is less than a capacitance threshold value $C_1$. In some embodiments, the capacitance threshold value $C_1$ can be an average or ideal capacitance of sensors of the same type. If the capacitance value C is less than the capacitance threshold value $C_1$ and if the uncorrected (or previously corrected) analyte concentration G4 is greater than an analyte concentration threshold $G_{th}$, then a capacitance correction function can be used to determine the correction factor $C_c$. If the capacitance value C is not less than the capacitance threshold value $C_1$ and/or if the uncorrected (or previously corrected) analyte concentration G4 is not greater than the analyte concentration threshold $G_{th}$, then the correction factor $C_c$ can be set to zero. For example, in one embodiment, the capacitance threshold value $C_1$ can be about 577 nanoFarad and the analyte concentration threshold $G_{th}$, e.g., a glucose concentration, can be about 100 mg/dL. Accordingly, if the capacitance value C and/or the analyte concentration G4 are with the predetermined range(s), the correction factor $C_c$ can be determined using a capacitance correction function, else the correction factor $C_c$ can be set to zero.

The capacitance correction function for calculating a capacitance correction factor $C_c$ when the measured capacitance value C is less than the capacitance threshold value $C_1$ and the uncorrected (or previously corrected) analyte concentration G4 is greater than an analyte concentration threshold $G_{th}$ can be in the form of Equation 29:

$$C_c = K_c(C_1 - C) \qquad \text{Eq. 29}$$

where $C_c$ is the correction factor, $K_c$ is an empirically derived constant (e.g., 0.051), $C_1$ is the capacitance threshold value (e.g., 577 nanoFarad), and C is the measured capacitance value.

After $C_c$ is calculated, e.g., using Equation 29, a couple of truncation functions can be performed to ensure that $C_c$ is constrained to a pre-determined range, thereby mitigating the risk of an outlier by limiting the maximum correction applied to the data. In one embodiment, if $C_c$ is greater than a cutoff value, $C_c$ can be set to the cutoff value. For example, a determination can be performed to determine whether $C_c$ is greater than a cutoff value, e.g., 5. If $C_c$ is greater than the cutoff value, e.g., 5, then $C_c$ is set to the cutoff value, e.g., 5. If $C_c$ is not greater than the cutoff value, then there generally is no need for truncation.

Once $C_c$ is determined, a capacitance corrected analyte concentration can be calculated. For example, a determination can be performed to determine whether the uncorrected (or previously corrected) analyte concentration G4 is less than an analyte concentration threshold $G_{th}$, e.g., 100 mg/dL if the analyte is glucose. If G4 is less than the analyte concentration threshold $G_{th}$, then no further correction is applied. If G4 is greater than the analyte concentration threshold $G_{th}$, then an Equation 30 can be used to calculate the capacitance corrected glucose concentration (or final concentration value) G5 by dividing $C_c$ by one hundred, adding one, and then multiplying by the analyte concentration [G]:

$$G5 = G4[1+0.01(C_c)]. \qquad \text{Eq. 30}$$

Once an analyte concentration is determined that has been corrected for the effects of age and/or storage, the analyte concentration can be outputted, e.g., to a display.

As discussed above, the systems and methods of the present invention can achieve an accuracy standard of at least ±10% for glucose concentrations above a glucose concentration threshold, such that at least 95% of a series of glucose concentration evaluations yield an glucose concentration value that is accurate to within 10% of a reference glucose measurement. In another exemplary embodiment, the method can achieve an accuracy standard of at least ±10 mg/dL for glucose concentrations below the glucose concentration threshold, such that at least 95% of a series of glucose concentration evaluations yield an glucose concentration value that is accurate to within about 10 mg/dL of a reference glucose measurement. For example, the glucose concentration threshold can be about 75 mg/dL. Applicants note that the algorithms and methods of the present invention can achieve these accuracy standards over a series of more than about 5,000 analyte concentration evaluations and also for more than about 18,000 analyte concentration evaluations. For example, the systems and methods of the present invention can meet or exceed the current U.S. Food and Drug Administration standards and recommendations for the accuracy of portable invasive blood glucose monitoring systems.

EXAMPLE 1

The reduction in donor-to-donor variation in glucose concentration measurements using the current summation time windows discussed above is demonstrated by this example. In the following example, the system included a sensor with two opposed electrodes, with reagents designed to react with the sample dried on one electrode. A plurality of samples from different donors was provided for analysis to test the performance of the systems, devices, and methods disclosed herein. The samples were 10,240 blood samples from 31 donors covering a hematocrit range of 37%-45%. Current transients were measured and analyzed using a first algorithm that relies on time windows from about 1.4 seconds to about 4.0 seconds for $i_l$ and from about 4.4 seconds to about 5 seconds for $i_r$. The measured current transients were also measured using a second algorithm discussed above, specifically the current values $i_r$ and $i_l$ calculated according to Eq. 15A and 15B, above. The standard deviation of the test results using the first algorithm was about 2.83. The standard deviation of the test results using the second algorithm shown and described herein was about 1.72. This result shows an unexpected improvement in accuracy when the current values $i_r$ and $i_l$ are calculated according to Eq. 15A and 15B.

EXAMPLE 2

The reduction in gender-to-gender variation in glucose concentration measurements using the current summation time windows discussed above is demonstrated by this example. In the following example, the system included a sensor with two opposed electrodes, with reagents designed to react with the sample dried on one electrode. A plurality of samples from 30 different donors, 15 male and 15 female, was provided for analysis to test the performance of the systems, devices, and methods disclosed herein. Current transients were measured and analyzed using a first algorithm, which included time windows from about 1.4 seconds to about 4.0 seconds for $i_l$ and from about 4.4 seconds to about 5 seconds for $i_r$. The measured current transients were also measured using a second algorithm discussed above, specifically the current values $i_r$ and $i_l$ calculated according to Eq. 15A and 15B, above.

Figure 9:
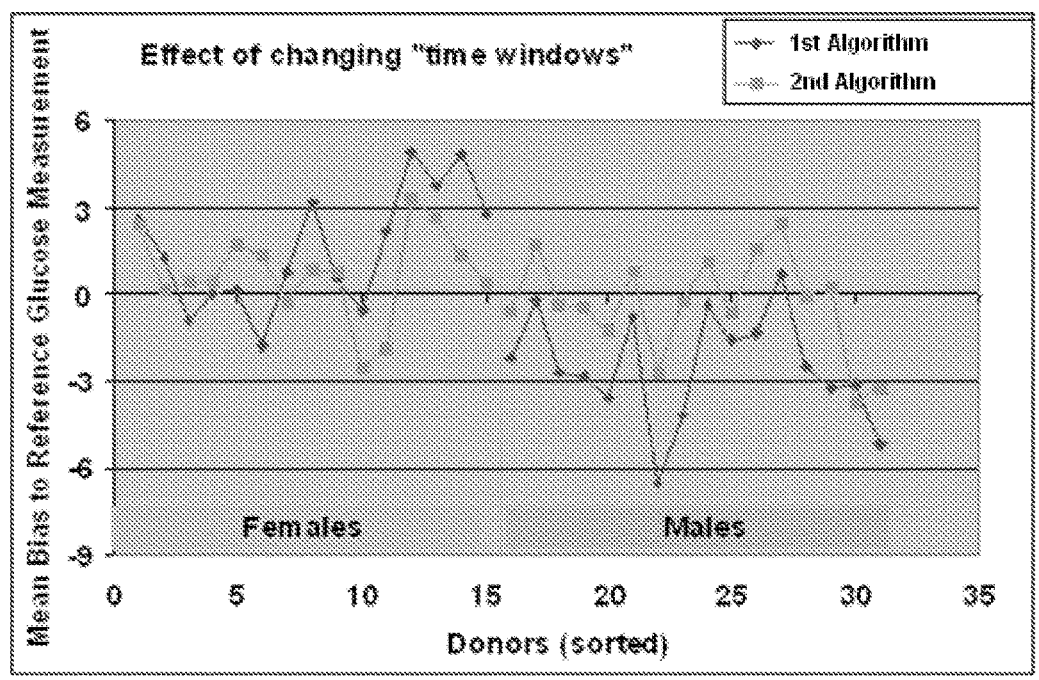
FIG. 9 is a chart showing the mean bias of blood samples from male and female donors using a first algorithm and a second algorithm disclosed herein.

As shown in FIG. 9, blood samples from females tend to have more positive bias from a reference glucose measurement made by a YSI 2700 clinical instrument (mean bias=1.6±2.1 SD) and blood samples from males tend to have more negative bias from a reference glucose measurement made by the YSI 2700 clinical instrument (mean bias=−2.5±1.9 SD). While not being limited to any particular theory, it is believed that one reason for the gender-to-gender differences is that the glucose oxidation kinetics are different in males and females (perhaps due to variations in the rate of glucose efflux in the blood cells, or differences in plasma viscosity). Applicants therefore tested various time windows for the current transients used to determine glucose concentration to determine time windows in which the observed differences were less apparent.

The time windows in the current transients that yielded the best results (i.e., lowest bias from reference glucose measurement) were the window from about 3.9 seconds to about 4.0 seconds for $i_l$ (see Eq. 15B, above) and the window from about 4.25 seconds to about 5 seconds for $i_r$ (see Eq. 15A, above). As illustrated in FIG. 9, these new time windows reduced the bias from reference glucose measurements made by the YSI 2700 clinical instrument for both male and female donors in comparison to the previous time windows, i.e., from about 1.4 seconds to about 4.0 seconds for $i_l$ and from about 4.4 seconds to about 5 seconds for $i_r$. In particular, the bias from reference glucose measurements made by the YSI 2700 clinical instrument was reduced to a mean bias of 0.7±1.6 SD for samples from female donors and a mean bias of −0.4±1.7 SD for samples from male donors. Thus for both genders, the mean bias was closer to zero and the SD bias was tighter when the time windows in Eqs. 15A and 15B were used.

EXAMPLE 3

The reduction in interference from urate concentration in glucose concentration measurements using the current summation time windows discussed above is demonstrated by this example. In the following example, the system included a sensor with two opposed electrodes, with reagents designed to react with the sample dried on one electrode. A plurality of samples were provided for analysis to test the performance of the systems, devices, and methods disclosed herein. Current transients were measured and analyzed using the a first algorithm, which included time windows from about 1.4 seconds to about 4.0 seconds for $i_f$ and from about 4.4 seconds to about 5 seconds for $i_r$. The measured current transients were also measured using a second algorithm shown and described herein, specifically the current values $i_r$ and $i_f$ calculated according to Eq. 15A and 15B. The bias from reference glucose measurements made by the YSI 2700 clinical instrument was determined for samples with a target plasma glucose level of 65, 240 or 440 mg/dL. These data were plotted against the concentration of urate which was spiked into the normal hematocrit blood. The slope of each line was calculated. A low slope shows low interference by urate. As shown in Table 1, below, the bias for the first algorithm was much higher than the bias for the second algorithm discussed above. More specifically, the current values $i_r$ and $i_f$ calculated according to Eq. 15A and 15B showed, surprisingly, 5-13 times less sensitivity to urate in blood than the first algorithm

TABLE 1

| [glucose] | delta bias per mg/dL interferent | |
|---|---|---|
| (mg/dL) | 1st Algorithm | 2nd Algorithm |
| 65 | −0.27 | 0.02 |
| 240 | −0.50 | −0.11 |
| 440 | −0.43 | −0.08 |

EXAMPLE 4

The effectiveness of the fill time correction algorithms disclosed herein for blood having high hematocrit is demonstrated by this example. In the following example, the system included a sensor with two opposed electrodes, with reagents designed to react with the sample dried on one electrode. A plurality of samples was provided for analysis to test the performance of the systems, devices, and methods disclosed herein. The samples were blood samples that contained a hematocrit range from about 15% to about 70%. The algorithms disclosed herein can compensate for the slow fill of blood and can accurately report glucose in hematocrits as large as 70%. This has consequences for the testing of neonates who can have very high hematocrits in the first 16 hours after birth. The glucose bias from reference glucose measurements made by the YSI 2700 clinical instrument was plotted against hematocrit. A slope of the best fit line to this data is an indication of the hematocrit-dependence of the glucose response. A small slope is more ideal. When the new time windows, specifically the current values $i_r$ and $i_f$ calculated according to Eq. 15A and 15B, above, are used to analyse data obtained with 15-70% hematocrit blood, then the slope of the bias versus hematocrit plot was −0.0278. When the fill time correction discussed above was included in the analysis then the slope decreases to −0.0098. Applicants surprisingly discovered that the fill time correction discussed above reduces the hematocrit-dependence of the glucose response by a factor of 2.8.

EXAMPLE 5

Improved shelf life of tests strips when using a capacitance correction algorithm according to the present invention is demonstrated by this example. Test strips are typically made with a hot melt adhesive between the two electrodes. If the sensors are stored at elevated temperatures for an extended period of time the adhesive can flow slowly and partially cover the electrodes. This will reduce the current measured when a voltage is applied. However, as the electrode area decreases the measured capacitance value will also decrease. The change in capacitance can be used to correct the glucose response, as described in the above equations.

A plot of bias versus storage time can be used to estimate the shelf life of the product (by noting the time at which the fitted line intersects one of the error budget limits). The capacitance correction described above only affects high glucose populations (>100 mg/dL).

In practice, a lower slope tends to correlate with a larger shelf life. When capacitance correction is not used, the slope of the bias versus storage time plot is −0.0559. However, when the data are corrected for changes in capacitance the slope of the bias versus storage time plot decreases to −0.0379. Therefore the product will have an approximately 50% longer shelf life when the capacitance correction algorithm discussed above are used to correct for changes in capacitance as the sensors age.

EXAMPLE 6

A higher overall accuracy resulting from the correction algorithms discussed above is demonstrated by this example. In the following example, the system included a sensor with two opposed electrodes, with reagents designed to react with the sample dried on one electrode. A plurality of samples from different donors was provided for analysis to test the performance of the systems, devices, and methods disclosed herein. The data set included 18,970 glucose assays, made up of:
  7,460 assays from a stability study (6 strip lots stored at 30° C./65% RH for 1-18 months, tested with normal hematocrit blood spiked to 50, 250 and 500 mg/dL plasma glucose),
  5,179 assays from temperature studies conducted between 5-45° C. (tested with normal hematocrit blood), and
  6,331 assays from hematocrit studies (15-70% hematocrit).

The data from these assays was analyzed using the algorithms discussed above. Fitting of the full algorithm to this "challenge superset" yielded the following fit parameters, which are discussed in relation to the equations disclosed above:

TABLE 2

| Parameter | Value |
|---|---|
| k (G-dep power term) | 1.24E−05 |
| p | 0.5246 |
| a | 0.03422 |
| zgr | 2.25 |
| AF offset | 2.88 |
| T (>15 C.) | −0.866 |
| TG (>15 C.) | 0.000687 |
| T (<15 C.) | −0.741 |
| TG (<15 C.) | 0.00322 |
| FT fact | 41 |
| Cap offset | 577 |
| Cap slope | 0.051 |

The stepwise improvement in the performance of the sensor with the addition of each aspect of the algorithm is shown in Table 3, below. The large dataset described above was fitted firstly with the new time windows only (G1), then with the fill time used to correct G1, then with the capacitance used to correct the previous result, then with the AF offset ("AFO") used to correct the previous result, and finally with the glucose dependent power term added in (to yield the full algorithm). This was done to show the incremental improvement provided by each step of the algorithm. The main changes are in the results obtained with G>75 mg/dL. The improvement in performance seen with each step of the algorithm. RMS bias is the root mean square bias between the calculated equivalent plasma glucose and the measured reference value. The bias is expressed with respect to a reference glucose concentration as mg/dL for G<75 mg/dL and as % for G>75 mg/dL. P10 refers to the percentage of glucose results which are within 10 mg/dL or 10% of the reference value.

TABLE 3

| Component of algorithm | RMS bias | P10 (G < 75 mg/dL) | P10 (G > 75 mg/dL) |
|---|---|---|---|
| New time windows | 4.51 | 99.33 | 95.30 |
| Fill time correction | 4.45 | 99.36 | 95.77 |
| Capacitance correction | 4.36 | 99.45 | 96.34 |
| Asymmetry factor offset | 4.27 | 99.49 | 96.70 |
| G-dependent power term | 4.25 | 99.49 | 96.89 |

The "asymmetry factor offset" and "glucose-dependent power term" were designed to overcome the tendency for the biases to be slightly positive at low glucose and slightly negative at high glucose. This non-ideal behaviour is regularly seen as a negative slope when bias is plotted against reference plasma glucose. The inclusion of the "asymmetry factor offset" and "glucose-dependent power term" in the algorithm reduced that negative slope by 26%. This change was sufficient to put an extra 1.55% of points within 10% of the reference plasma glucose value when the glucose level was greater than 80 mg/dL.

The breakdown in results by dataset is shown in Table 4. In every case P10>95%, which satisfies the preferred performance criteria of the American Diabetes Association.

TABLE 4

| Dataset | RMS bias | P10 (G < 75 mg/dL) | P10 (G > 75 mg/dL) | Count |
|---|---|---|---|---|
| Hematocrit | 3.88 | 99.25 | 97.92 | 6331 |
| Stability | 4.25 | 99.64 | 96.98 | 7460 |
| Temperature | 4.67 | 99.51 | 95.51 | 5179 |

Figure 10:
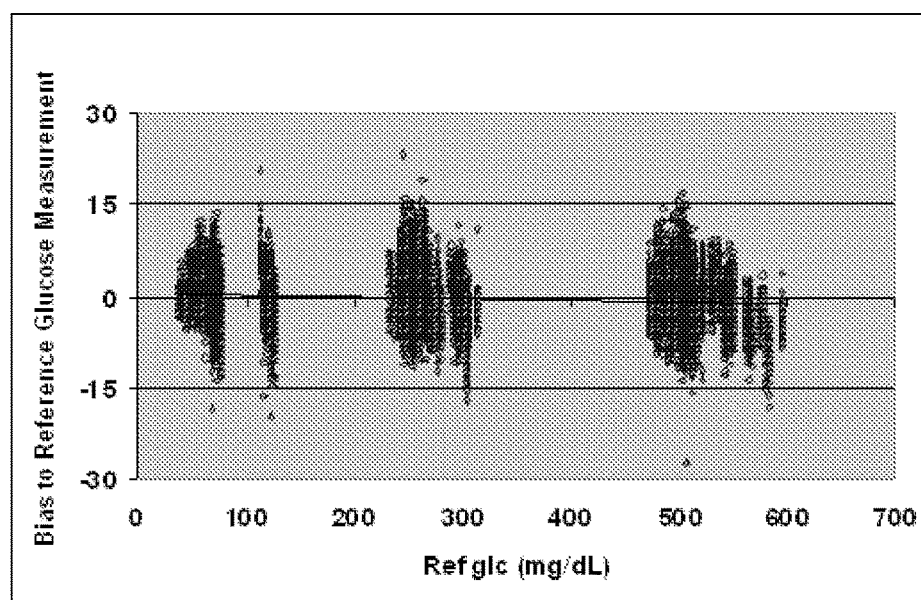
FIG. 10 illustrates a plot of bias from a reference glucose measurement against the reference glucose measurement for each member of a data set including approximately 18,970 glucose assays.
Figure 11:
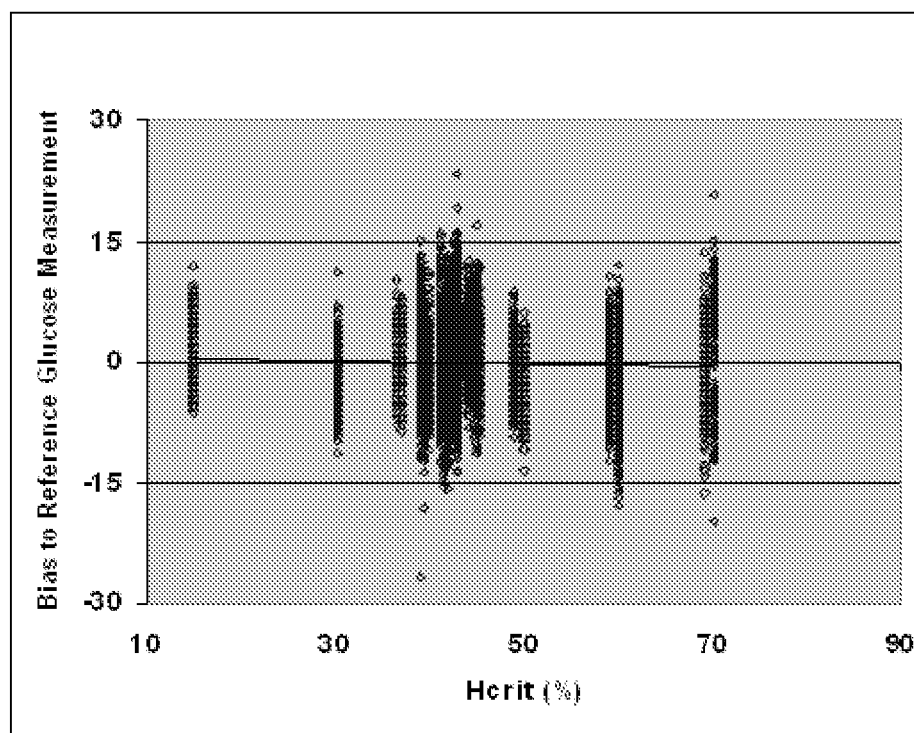
FIG. 11 illustrates a plot of bias from a reference glucose measurement against the hematocrit percentage for each member of a data set including approximately 18,970 glucose assays.
Figure 12:
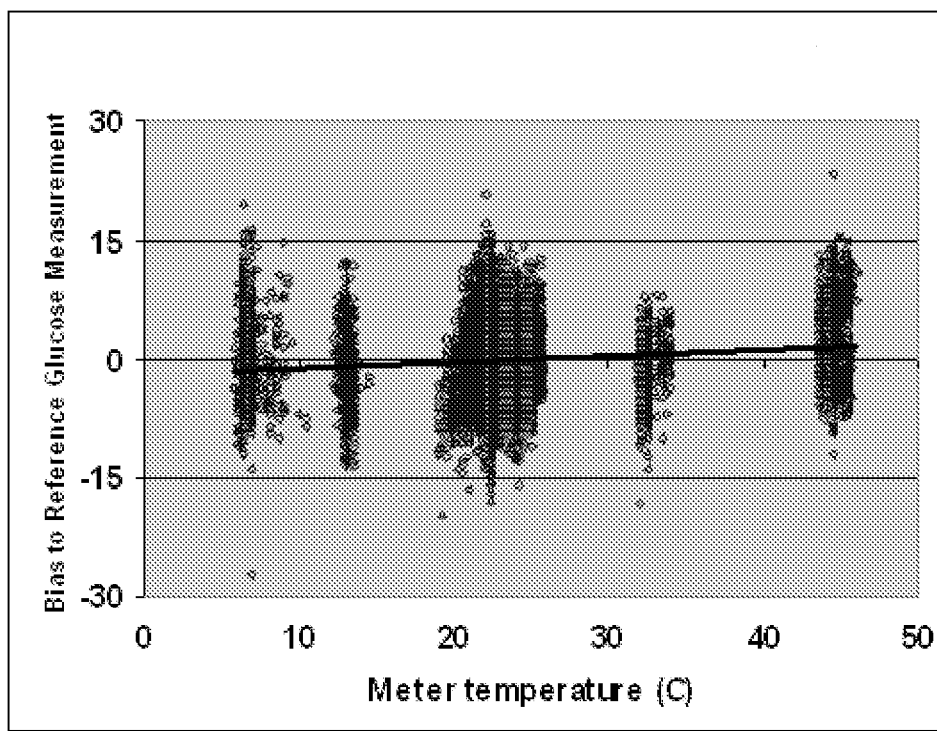
FIG. 12 illustrates a plot of bias from a reference glucose measurement against the a temperature measurement for each member of a data set including approximately 18,970 glucose assays.
Figure 13:
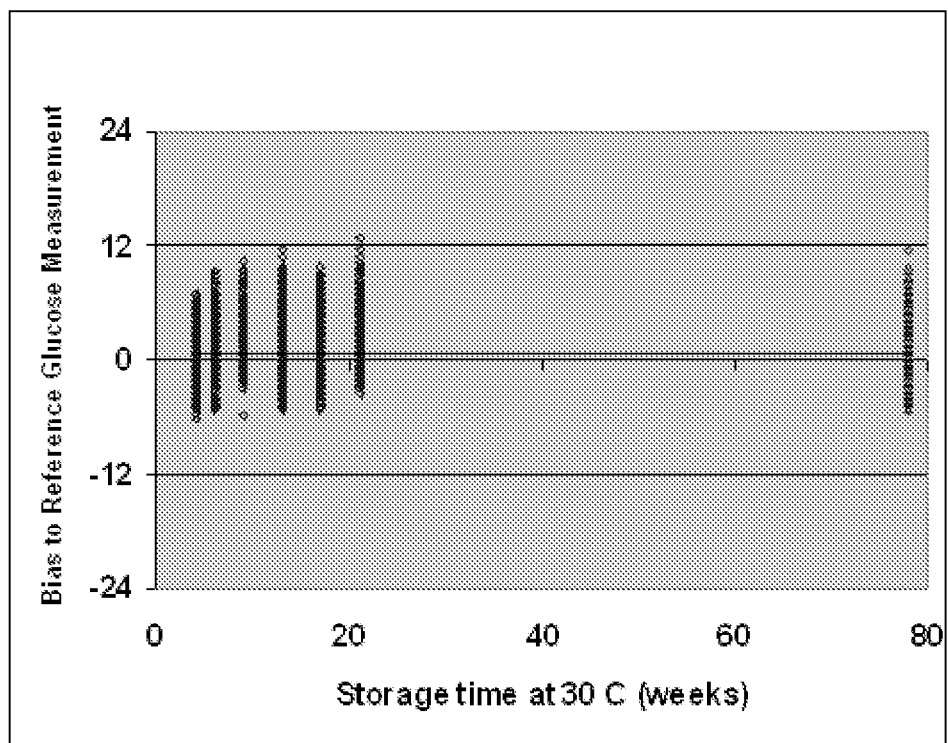
FIG. 13 illustrates a plot of bias from a reference glucose measurement against test strip storage time for members of a data set in which the glucose concentration was less than about 75 mg/dL.
Figure 14:
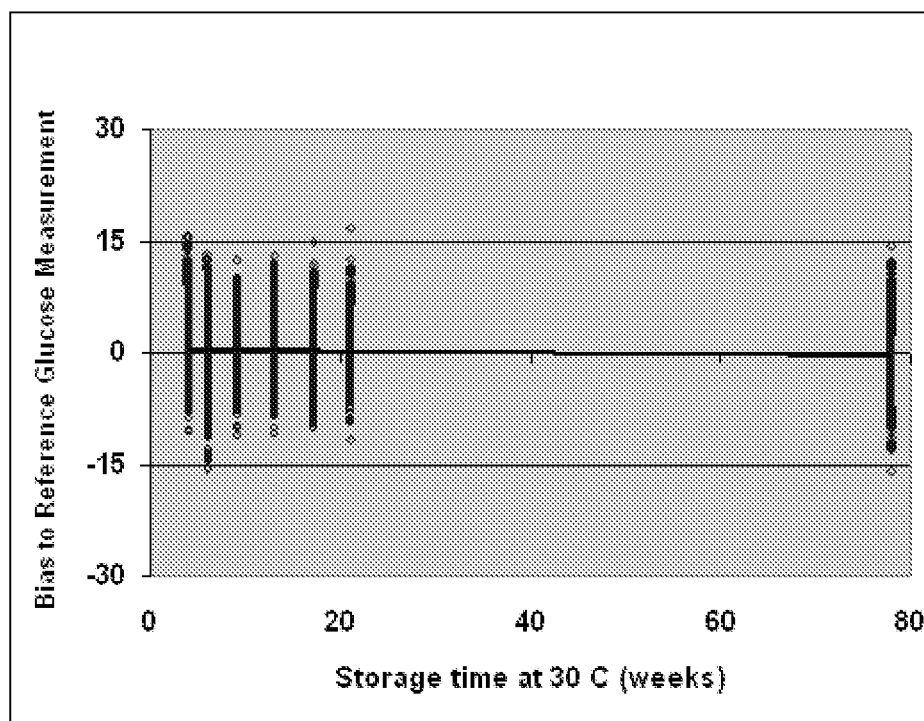
FIG. 14 illustrates a plot of bias from a reference glucose measurement against test strip storage time for members of a data set in which the glucose concentration was greater than about 75 mg/dL.

The results are also presented graphically in FIGS. 10-14, to allow an assessment of outliers which do not fall within 10 mg/dL or 10% of the reference plasma glucose value. FIGS. 10-12 show the full dataset plotted against reference glucose, hematocrit and temperature. FIGS. 13-14 show the stability data split as G<75 mg/dL and G>75 mg/dL.

While the invention has been described in term is of particular variations and illustrative figures, one skilled in the art will recognize that the invention is not limited to the variations or figures described. In addition, where methods and steps described above indicate certain events occurring in certain order, those skilled in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. All publications and references cited herein are expressly incorporated herein by reference in their entirety.

What is claimed is:

1. A method of determining an analyte concentration in a sample, the method comprising:
    detecting a sample including an analyte introduced to an electrochemical sensor, the electrochemical sensor comprising two electrodes in a spaced apart configuration;
    reacting the analyte to cause a physical transformation of the analyte between the two electrodes;
    measuring current outputs at discrete intervals to derive a fill time of the sample in the sensor and a capacitance of the electrochemical sensor with the sample;
    determining a first analyte concentration value from the current outputs;
    calculating a second analyte concentration value from the current outputs and the first analyte concentration value;
    correcting the second analyte concentration value for temperature effects to provide for a third analyte concentration value;
    correcting the third analyte concentration value as a function of the fill time of the sensor to provide for a fourth analyte concentration value; and
    correcting the fourth analyte concentration value as a function of the capacitance to provide for a final analyte concentration value in which the current outputs measured at discrete intervals comprise a first current summation $i_r$ and a second current summation $i_l$ where:

$$i_r = \sum_{t=4.25}^{5} i(t)$$

and $$i_l = \sum_{t=3.9}^{4} i(t)$$

where i(t) comprises the absolute value of the current measured at time t.

2. The method of claim 1, in which the step of determining the first analyte concentration value includes calculating an analyte concentration G1 with an equation of the form:

$$G1 = \left(\frac{i_r}{i_l}\right)^p \{ai_2 - zgr\}$$

where p is about 0.5246; a is about 0.03422; $i_2$ comprises an antioxidant-corrected current value; and zgr is about 2.25.

3. The method of claim 1, in which the step of calculating the second analyte concentration value includes calculating an analyte concentration G2 with an equation of the form:

$$G2 = \left(\frac{i_r}{i_l} - AFO\right)^{\{p+kG1\}} \{ai_2 - zgr\}$$

where p is about 0.5246; a is about 0.03422; $i_2$ comprises an antioxidant-corrected current value; AFO comprises is about 2.88; zgr is about 2.25; and k is about 0.0000124.

4. The method of claim 1, in which the third analyte concentration value comprises a first temperature correction to the second analyte concentration value whenever an ambient temperature is greater than a first temperature threshold and a second temperature correction whenever the ambient temperature is less than or equal to the first temperature threshold.

5. The method of claim 1, in which the step of correcting the third analyte concentration value as a function of the fill time of the electrochemical sensor comprises calculating a fill time correction factor based on the fill time, wherein the fill time correction factor is about zero when the fill time is less than a first fill time threshold; the fill time correction factor is calculated based on the fill time when the fill time is greater than the first fill time threshold and less than a second fill time threshold; and the fill time correction factor comprises a constant value when the fill time is greater than the second fill time threshold; and correcting the fourth analyte concentration value as a function of the capacitance to provide for a final analyte concentration value.

6. The method of claim 5, in which the first fill time threshold is about 0.2 second and the second fill time threshold is about 0.4 second.

7. The method of claim 6, in which the fourth analyte concentration value equals the third analyte concentration value when the third analyte concentration value is less than about 100 mg/dL; and the fourth analyte concentration value comprises a product of the third analyte concentration value, with an offset to the fill time correction factor when the third analyte concentration value is greater than about 100 mg/dL.

8. The method of claim 1, in which the final analyte concentration value is set to equal to the fourth analyte concentration value when the fourth analyte concentration value is less than a first concentration threshold.

9. The method of claim 1, in which the final analyte concentration value comprises a product of a capacitance correction factor and the fourth analyte concentration value when the fourth analyte concentration value is greater than a first concentration threshold, the capacitance correction factor for the final analyte concentration value being based on a measured capacitance when the capacitance is less than a first capacitance threshold and the capacitance correction factor is set to a maximum value when the capacitance correction factor is greater than a set value.

10. A method of obtaining increased accuracy of a test strip, the method comprising:
providing a batch of test strips with each test strip having a reaction chamber, the reaction chamber including two electrodes spaced apart with a reagent disposed therebetween, and further comprising one or more adhesive layers;
introducing a referential sample containing a referential concentration of an analyte to each of the batch of test strips;
reacting the analyte to cause a physical transformation of the analyte between the two electrodes;
measuring current outputs at discrete intervals to derive a fill time of the referential sample into the test strip and a capacitance of the test strip with the referential sample, the capacitance being a function of a slow flow of the one or more adhesive layers into the reaction chamber based on the age or storage condition of the test strip;
determining a first analyte concentration value from the current outputs;
calculating a second analyte concentration value from the current outputs and the first analyte concentration;
correcting the second analyte concentration value for temperature effects to provide for a third analyte concentration value;
correcting the third analyte concentration value as a function of the fill time of the sensor to provide for a fourth analyte concentration value; and
correcting the fourth analyte concentration value as a function of the capacitance to provide for a final analyte concentration value for each of the batch of test strips, in which the final analyte concentration value is set to equal to the fourth analyte concentration value when the fourth analyte concentration value is less than a first concentration threshold, wherein at least 95% of the final analyte concentration values of the batch of test strips are within 10% of the referential analyte concentration.

11. An analyte measurement device comprising:
a housing;
a strip port connector mounted on the housing and configured to receive an analyte test strip; and
a microprocessor disposed in the housing, the microprocessor being connected to the strip port connector, a power supply and a memory such that when an analyte test strip is coupled to the strip port with a sample deposited in a test chamber of the test strip, the analyte is caused to react between two electrodes and provide for a first analyte concentration estimate G1 based on measured output current values over discrete intervals during a reaction of the analyte, a second analyte concentration estimate G2 based on measured output current values over discrete intervals during a reaction of the analyte, a temperature corrected analyte concentration value G3 from the second analyte concentration value G2, a sample fill time corrected analyte concentration value G4 from the temperature corrected analyte concentration G3, and a test strip capacitance corrected final concentration value G5 from the sample fill-time corrected analyte concentration value G4 in which the discrete intervals comprise a first interval from about 3.9 seconds to about 4 seconds and a second interval from about 4.25 seconds to about 5 seconds, the first and second intervals being measured from the time a sample is deposited in the test chamber, such that the output current values measured over the first and second intervals comprise a first current summation $i_r$ and a second current summation $i_l$ where $$i_r = \sum_{t=4.25}^{5} i(t)$$

and $$i_l = \sum_{t=3.9}^{4} i(t)$$

where $i(t)$ comprises the absolute value of the current measured at time t.

12. The device of claim 11, in which the first analyte concentration value G1 comprises derivation of the current values with an equation of the form:

$$G1 = \left(\frac{i_r}{i_l}\right)^p \{ai_2 - zgr\}$$

where p is about 0.5246; a is about 0.03422; $i_2$ comprises an antioxidant-corrected current value; and zgr is about 2.25.

13. The device of claim 12, in which $i_2$ further comprises an equation of the form:

$$i_2 = i_r\left(\frac{i(4.1) - 2i(1.1) + i_{ss}}{i(4.1) + i_{ss}}\right)$$

where i(4.1) is an absolute value of the current during a third electric potential; i(1.1 is an absolute value of the current during a second electric potential; and $i_{ss}$ is a steady-state current.

14. The device of claim 12, in which $i_{ss}$ comprises an equation of the form:

$$i_{ss} = \frac{i(5)}{1 + 4e^{-4\pi^2 D/L^2}}$$

where i(5) is an absolute value of the current during a third electric potential; π is a constant; D is a diffusion coefficient of a redox species, and L is a distance between the two electrodes.

15. The device of claim 11, in which the second analyte concentration value G2 comprises derivation with an equation of the form:

$$G2 = \left(\frac{i_r}{i_l} - AFO\right)^{\{p+kG1\}} \{ai_2 - zgr\}$$

where p is about 0.5246; a is about 0.03422; $i_2$ comprises an antioxidant-corrected current value; AFO is about 2.88; zgr is about 2.25; and k is about 0.0000124.

16. The device of claim 11, in which the temperature corrected analyte concentration value G3 is corrected by a fill time correction factor based on a fill time, the fill time correction factor is about zero when the fill time is less than a first fill time threshold and when the fill time is greater than the first fill time threshold and less than a second fill time threshold, the fill time correction factor is calculated based on the fill time, and when the fill time is greater than the second fill time threshold, the fill time correction factor comprises a constant value.

17. The device of claim 16, in which the first fill time threshold is about 0.2 second and the second fill time threshold is about 0.4 second.

18. The device of claim 16, in which the temperature corrected analyte concentration value G3 is a first temperature correction to the second analyte concentration value G2 whenever an ambient temperature is greater than first temperature threshold and a second temperature correction whenever the ambient temperature is less than or equal to the first temperature threshold.

19. The device of claim 18, in which the sample fill time corrected analyte concentration value G4 is the temperature corrected analyte concentration value G3 when the temperature corrected analyte concentration value G3 is less than about 100 mg/dL and the sample fill time corrected concentration value G4 is a percentage increase in the temperature corrected analyte concentration value in view of the fill time correction factor when the temperature corrected analyte concentration value G3 is greater than about 100 mg/dL.

20. The device of claim 11, in which the test strip capacitance corrected final concentration value G5 is set equal to the sample fill time corrected analyte concentration value when the sample fill-time corrected analyte concentration value G4 is less than a first concentration threshold.

21. The device of claim 11, in which the test strip capacitance corrected final concentration value G5 is a product of a capacitance correction factor and the sample fill time corrected analyte concentration value G4 when the sample fill time corrected analyte concentration value G4 is greater than a first concentration threshold, the capacitance correction factor for the corrected final concentration value G5 being based on a measured capacitance when the capacitance is less than a first capacitance threshold and the capacitance correction factor is set to a maximum value when the capacitance correction factor is greater than a set value.

* * * * *

UNITED STATES PATENT AND TRADEMARK OFFICE
CERTIFICATE OF CORRECTION

PATENT NO. : 9,632,054 B2
APPLICATION NO. : 13/824308
DATED : April 25, 2017
INVENTOR(S) : Ronald C. Chatelier et al.

It is certified that error appears in the above-identified patent and that said Letters Patent is hereby corrected as shown below:

On the Title Page

Item (56) References Cited:
U.S. PATENT DOCUMENTS change "1,455,258 A1" to --6,945,943 B2--

In the Claims

Correction to Claim 13 is requested as follows:
Column 45 Line 16, please change "electric potential; i(1.1 is an absolute value of the current" to
--electric potential; i(1.1) is an absolute value of the current--

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*